(12) United States Patent
Beekman

(10) Patent No.: US 8,198,594 B2
(45) Date of Patent: Jun. 12, 2012

(54) RADIATION DETECTION DEVICE, SCINTILLATION DEVICE AND DETECTION METHOD, AS WELL AS MULTIPLE IMAGE-FORMING DEVICE

(75) Inventor: Frederik Johannes Beekman, Utrecht (NL)

(73) Assignee: Milabs B.V., Utrecht (NL)

( * ) Notice: Subject to any disclaimer, the term of this patent is extended or adjusted under 35 U.S.C. 154(b) by 518 days.

(21) Appl. No.: 12/083,383

(22) PCT Filed: Oct. 11, 2006

(86) PCT No.: PCT/NL2006/000513
§ 371 (c)(1),
(2), (4) Date: Feb. 9, 2009

(87) PCT Pub. No.: WO2007/043868
PCT Pub. Date: Apr. 19, 2007

(65) Prior Publication Data
US 2009/0242775 A1 Oct. 1, 2009

(30) Foreign Application Priority Data

Oct. 11, 2005 (NL) .................................... 1030168
Oct. 11, 2005 (NL) .................................... 1030169
Oct. 12, 2005 (NL) .................................... 1030179

(51) Int. Cl.
*G01T 1/166* (2006.01)
(52) U.S. Cl. .............................. 250/363.04; 250/370.11
(58) Field of Classification Search ............. 250/363.04, 250/370.11
See application file for complete search history.

(56) References Cited

U.S. PATENT DOCUMENTS 3,825,758 A * 7/1974 Miraldi ......................... 250/366
(Continued)

FOREIGN PATENT DOCUMENTS

EP 0 273 670 A 7/1988
(Continued)

OTHER PUBLICATIONS

Beekman, F J et al., Journal of Nuclear Medicine Soc. Nucl. Med., vol. 46, No. 7, Jul. 2005, pp. 1194-1200.

*Primary Examiner* — David Porta
*Assistant Examiner* — Djura Malevic
(74) *Attorney, Agent, or Firm* — Birch, Stewart, Kolasch & Birch, LLP

(57) ABSTRACT

The invention provides a radiation detection device (1) for obtaining an image of a part of a test animal or human using high-energy radiation, comprising a detection chamber, a plurality of pinholes distributed all around the detection chamber over at least one pinhole wall, at least one framing wall having an opening for the high-energy radiation, at least one detector which is designed for detecting high-energy radiation, in which a plurality of image fields are provided on the at least one detector, in each case having one beam path from a part of the detection chamber to at least one detector, in which at least one of the at least one pinhole wall and the at least one framing wall is displaceable in such a manner that at least one of the plurality of image fields can be modified in size and/or direction. This provides the possibility to image an object at several angles, or to image a larger or a different part thereof, so that the entire device can be used in a more flexible manner.
The invention also provides a scintillation device and detection method, as well as a multiple image-forming device.

28 Claims, 6 Drawing Sheets

U.S. PATENT DOCUMENTS

| | | | |
|---|---|---|---|
| 3,840,747 A | 10/1974 | Macovski | |
| 4,823,016 A * | 4/1989 | Yamashita et al. | 250/363.03 |
| 4,870,280 A * | 9/1989 | Yamashita et al. | 250/368 |
| 5,118,934 A * | 6/1992 | Hailey et al. | 250/366 |
| 5,391,877 A | 2/1995 | Marks | |
| 5,506,408 A | 4/1996 | Vickers et al. | |
| 5,567,944 A * | 10/1996 | Rohe et al. | 250/370.09 |
| 6,528,796 B1 * | 3/2003 | Kaifu et al. | 250/370.11 |
| 7,238,946 B2 * | 7/2007 | Joung et al. | 250/369 |
| 7,323,688 B2 * | 1/2008 | Joung | 250/363.02 |
| 7,847,260 B2 * | 12/2010 | Inbar | 250/370.11 |
| 2002/0070365 A1 * | 6/2002 | Karellas | 250/581 |
| 2003/0030003 A1 * | 2/2003 | Maekawa et al. | 250/367 |
| 2004/0232348 A1 | 11/2004 | Beekman | |
| 2005/0205796 A1 * | 9/2005 | Bryman | 250/370.11 |
| 2006/0202125 A1 * | 9/2006 | Suhami | 250/368 |
| 2008/0067390 A1 * | 3/2008 | Ramsden et al. | 250/361 R |

FOREIGN PATENT DOCUMENTS

| | | |
|---|---|---|
| NL | 1021554 A | 9/2002 |

* cited by examiner

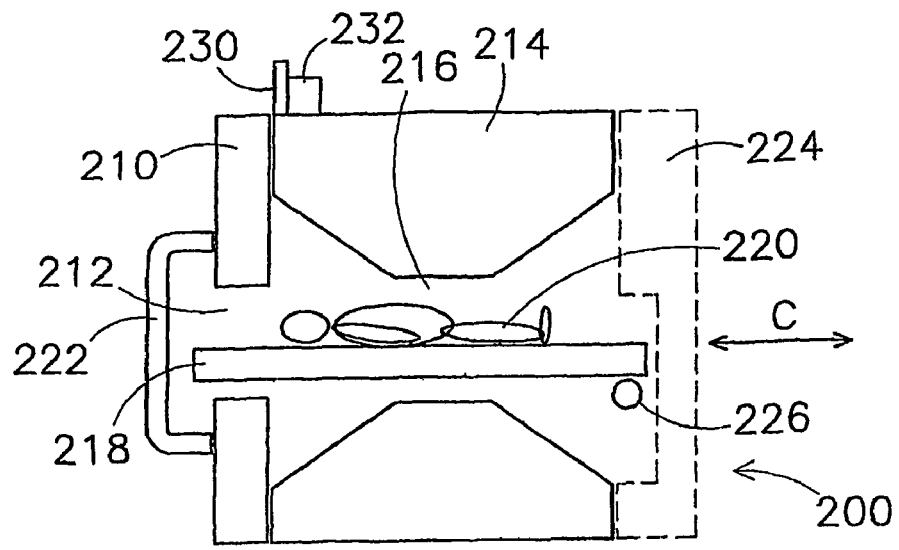
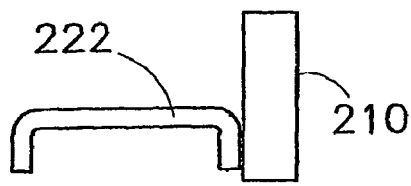
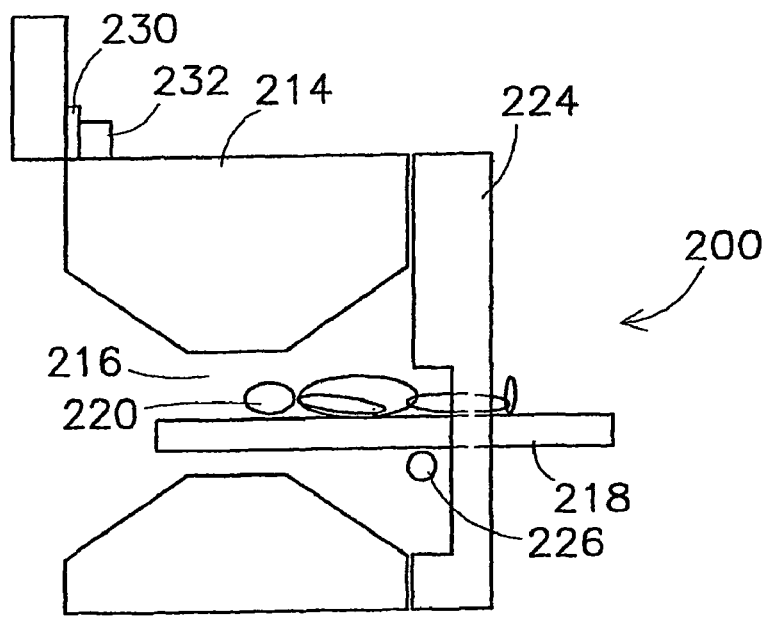
Fig 8a
Fig 8b

RADIATION DETECTION DEVICE, SCINTILLATION DEVICE AND DETECTION METHOD, AS WELL AS MULTIPLE IMAGE-FORMING DEVICE

In a first aspect, the present invention relates to a radiation detection device, in particular to a radiation detection device for obtaining an image of a part of a test animal or human using high-energy radiation, comprising a detection chamber, a plurality of pinholes distributed all around the detection chamber over at least one pinhole wall, at least one framing wall having an opening for the high-energy radiation, at least one detector which is designed for detecting high-energy radiation, in which a plurality of image fields are provided on the at least one detector, in each case having a beam path from a part of the detection chamber to at least one detector.

The article U-SPECT-I: A Novel System for Submillimeter-Resolution Tomography with Radiolabeled Molecules in Mice, by F. J. Beekman et al., describes a system for tomography comprising a measuring chamber in the shape of a space formed by a pinhole tube, a triangular arrangement of the detectors as well as a tube placed between them with holes which limit the image fields of the pinholes to form non-overlapping projection image fields.

One drawback of such a system is that it offers limited flexibility, in the sense that the image field of the detectors has fixed boundaries, both in terms of the object space, that is to say the part of the three-dimensional object space which is imaged, and of the projection image space, that is to say of the two-dimensional projections of the object space on the detectors.

It is an object of the first aspect of the present invention to provide a radiation detection device which is relatively flexible during operation. In particular, it is desirable to provide a radiation detection device which has a variable image field, with which it becomes possible to scan, for example, relatively large animals, or, for example, to image the area surrounding a relevant central research region at several angles in order to be able to produce a good reconstruction of the surrounding area.

This object is achieved according to the first aspect of the invention with a radiation detection device, which is characterized in that at least one of the at least one pinhole wall and the at least one framing wall is displaceable in such a manner that at least one of the plurality of image fields can be modified in size and/or direction.

By making the pinhole wall and the framing wall displaceable in this manner, it becomes possible to modify an image field. This means in particular that a different beam path is provided between one part of the detection chamber and the one or more detectors. Of course, this means that another part of the detection chamber can be imaged. This also creates the possibility of imaging, for example, the surrounding area of a research area (as well), or simply a research area with a larger diameter. An example which may be mentioned in this context is brain research using high resolution with a position of the pinhole wall(s) and of the framing wall(s) such that the images on the detectors do not overlap, while another image can be formed in which the positions have been modified and the projection image fields on the detectors have become so large that they overlap. The latter is not an aim in itself, but may be the result of the desire and the possibilities to image relatively large or other parts of the detection chamber.

It should be stressed that the expression "all around" should be interpreted as: "occupying a solid angle, viewed from the detection chamber". In this case, it is certainly not necessary to form a completely continuous surface, i.e. a complete 4π solid angle about the detection chamber. Also, "all around" should therefore not be limited to "entirely all around", but for example also includes the situation where the pinholes only occupy a limited (solid) angle around the detection chamber. The same logic applies to the framing wall(s). All this will be explained in more detail below.

In addition, it should also be mentioned that the term high-energy radiation is understood to mean the radiation which is used in radiology, such as gamma radiation from radioactive substances, etc. Furthermore, a detector having a plurality of image fields may be provided, or a plurality of detectors each having one or more image fields.

It should be noted here that said article also presents a system without the screening cylinder with holes which prevent overlap of the image fields. In this system, the image fields (partially) overlap resulting in a relatively large image field and a relatively large total sensitivity, albeit with a loss of information, precisely due to the patterns overlapping on the detectors. Although in some cases this system may have certain advantages compared to the previously described prior art system, this system is not flexible during operation either. In addition, the device according to the invention, that is to say with variable image field(s), offers the possibility of combining the advantages of both systems. For example, it is possible to carry out both a part measurement where the image fields on the detectors do not overlap and a part measurement with other image fields, which may, for example, overlap during one and the same measurement. This then forms a dynamic apparatus in which the combination of projection images at different position settings offers a great advantage.

Although normally information is lost when images overlap, as it is impossible to determine per se whether a photon which is captured belongs to one or the other image field, it is exactly the combination of, for example, a measurement with non-overlapping image fields and a measurement with overlapping image fields which makes it possible to nevertheless collect this information, at least to a large extent. After all, it is possible to use the results of the measurement with non-overlapping image fields as a basis for processing the results of the measurement with overlapping images. In practice, such images can be processed using reconstruction techniques, for example based on calibration measurements. Such calibration measurements may include, for example, measurements using point sources, where a point source is displaced through the detection chamber and in each case an image is captured with the detectors. The source is of a known intensity, and thus it is possible to compile matrices with which it is possible to calculate the distribution of the intensity in the test animal and the like for subsequent images. In other words, the strength of the first aspect of the present invention is the possibility to combine images under different recording conditions, in particular both non-overlapping and overlapping images, or different sets of non-overlapping images.

In principle, the detection chamber can have any desired shape. In practice, however, a particular embodiment is characterized by a cylindrical detection chamber. In this embodiment, the plurality of pinholes and the like are distributed all around the detection chamber. Alternatively, a non-cylindrical detection chamber with a constant diameter is also possible, or also a (hemi)spherical detection chamber, etc. In the case of a cylindrical detection chamber surrounded by a plurality of pinholes, there is often a central detection region, which is formed in principle by the overlap of all fields of view of all pinholes. This is dependent on the arrangement of the pinholes, but is generally a central circular-symmetrical part of the detection chamber. Usually, the one or more framing walls in this case ensure that the image fields on the detector(s) of the radiation detection device do not overlap by blocking a portion of the field of view of the pinhole. In this case, the one or more framing wall(s) may be situated between the pinhole wall(s) and the detector(s), and this is often preferable in view of the small distance between pinhole and source, and/or between the source and the pinhole wall(s).

In the context of the present invention, an "opening" in the framing wall is understood to mean not only a through-hole, but also a recess, space or the like in the framing wall, such as a crenelation or the like. The framing wall comprises such openings, recesses, etc. in order to "frame" the high-energy radiation in image fields for the detectors. Such a framing wall comprises at least one layer of a material which substantially blocks the high-energy radiation, such as lead, gold, tungsten, etc.

According to the invention, it is possible to modify at least one of the plurality of image fields in terms of size and/or direction using the radiation detection device. This can be achieved, for example, by enlarging or reducing the openings in the framing wall, or by moving them relative to, for example, the detectors or the pinholes of the pinhole wall. If the framing wall is rotated through an angle about, for example, its longitudinal axis, or at least an axis of rotation, it is, for example, possible for the dimensions of the image fields to remain substantially unchanged, and thus, for example, to remain non-overlapping, but for the viewing direction to be modified. A particular embodiment of the radiation detection device according to the invention is characterized in that the at least one of the at least one pinhole wall and the at least one framing wall is displaceable while an image is being obtained with the radiation detection device. As has already been indicated above, the possibility to combine measurements at different positions in the pinhole wall and/or framing wall is an advantage of the present invention. This comprises both the possibility of measurements during constant movement, that is to say displacement, and a combination of part measurements between which part measurements at least one pinhole wall and/or at least one framing wall is displaced. In particular, at least one pinhole wall and/or at least one framing wall is installed in the radiation detection device so as to be slidable and/or rotatable. This provides the possibility of simple displacements during a measurement. Advantageously, at least one motor is provided for displacing the pinhole wall and/or the framing wall.

A particular embodiment is characterized in that the at least one framing wall is at least partially retractable from a beam path. During this at least partial, and preferably complete, retraction of the framing wall from the beam path, a partial, preferably complete, maximum enlargement of the image field or the image fields is created. In this manner, as large a part of the detection chamber as possible is available in the shape of in each case the complete field of vision of the pinhole for measuring, that is to say for producing images. Preferably, the at least one framing wall comprises a mechanism for retraction from the beam path. Such a mechanism may, for example, comprise an adjusting screw, guide rail or the like, as well as a motor for retracting the framing wall, if desired.

It is also possible to provide the framing wall with a locking mechanism with which the framing wall can be secured in a position, preferably in several positions.

In one embodiment, at least one framing wall and/or one pinhole wall comprises a flat or curved panel. A framing wall and/or pinhole wall of this type can also be satisfactory, for example by being displaced relative to one another, relative to the detection chamber or relative to the source inside the latter. The pinhole wall and/or framing wall may be rotatable around the detection chamber. This may be achieved, for example, by providing it/them with a guide and optionally a motor for driving it/them. In fact, it is thus possible to create a simulation of a framing and/or pinhole wall which is closed all around by moving the relevant wall(s) around the detection chamber. Thus, measurements can be carried out at various angles and a complete three-dimensional image can be produced.

In a particular embodiment, at least one panel comprises a continuous surface around the detection chamber. Of course, this surface may have holes, but an uninterrupted circuit around the detection chamber is possible. The continuous surface is preferably a cylinder or a polygon. A cylinder provides optimum rotational symmetry, and a polygon, for example and in particular a triangle, square, pentagon or hexagon, provides flat portions behind which detectors can be placed in an expedient manner.

A particular radiation detection device comprises a plurality of framing walls all around the detection chamber. By providing a plurality of framing walls, the number of possibilities of delimiting image fields is expanded. It should be noted here that the term image field as used in the present document may refer to a "surface on the detector where an image is formed" as well as to a "part of the detection chamber which is imaged on said surface on the detector" and to a "solid angle associated with a beam path between said part of the detection chamber and said surface on the detector". Unless indicated otherwise, these three concepts are used interchangeably in the present document. For example, the first concept is also referred to as "projection image field" and the two last-mentioned concepts are also referred to as "field of view of the pinhole" or "object image field".

Preferably, the plurality of framing walls are positioned around the detection chamber substantially concentrically. In the present document, the expression "substantially concentrically" is understood to mean that the corresponding components etc. have centre points and/or central axes, all of which fall within the innermost of the concentric components and the like, and preferably coincide. Positioning the plurality of framing walls substantially concentrically around the detection chamber creates an interesting advantage, namely that the openings in the individual framing walls can interact in such a way that new, smaller, as it were "net", openings are created. Such substantially concentrically positioned framing walls may, for example, be cylindrical, but this is not imperative. The framing walls may for example also be triangular, square etc. in section, with identical cross section along a length, if the framing walls are displaced substantially only in a direction parallel to their longitudinal axis.

In particular, the openings in the framing walls comprise at least two, and in particular two, substantially parallel edge parts. Advantageously, the edge parts extend from a hole in one of the plurality of framing walls in a first direction and the edge parts of an opening associated with said opening in another, concentrically positioned framing wall extend in a second direction which is substantially perpendicular to the first direction. As the "net" opening in this way comprises two sets of parallel edge parts as a result of the common framing walls, a substantially rectangular net-opening is created. Such a rectangular opening, in particular several such rectangular openings, is advantageous when detector surfaces are to be used efficiently. Of course, it is also possible to create openings of different shapes. An additional advantage of said embodiment is that the individual openings in the framing walls can be created in a very simple manner, by for example connecting some bore holes and milling holes. Of course, any other desired technique of creating openings in the framing wall can also be used, for example laser cutting and the like. Therefore, such a rounded opening should not be seen as limiting. The only thing that should be noted is that it is not important whether the finish of corners of openings in the framing wall is accurate, if the "net" openings are made up of two or more openings, as a smooth finish of two parallel edge parts can easily be achieved.

Preferably, at least two of the plurality of framing walls are displaceable relative to one another, preferably concentrically rotatable or slidable. This offers the possibility of altering the interaction between openings in different framing walls. In other words, the "net" opening which is formed by two or more openings associated and interacting with one another in different framing walls can be changed in respect of size and/or position relative to the detector. This results in the image field being modified accordingly.

In a particular embodiment, at least one framing wall comprises at least one opening with adjustable dimensions. In this embodiment, it is possible to change the dimensions of an opening itself, for example by means of displaceable slides, a diaphragm or the like. This offers the advantage that in principle only one framing wall is required. Both with this and with all other embodiments of the radiation detection device according to the present invention, a particular embodiment of a described technical feature which relates to at least one opening is characterized in that said technical feature relates to all openings. A similar consideration applies in respect of the at least one framing wall and the at least one pinhole wall.

A particular embodiment is characterized in that at least one framing wall comprises one or more elongate holes extending substantially in one direction, and in that at least one other framing wall comprises one or more elongate holes extending substantially in a different direction. When positioned correctly, that is to say when the at least one framing wall and the at least one other framing wall at least partially overlap, "net" holes are thus created, which more or less a projection of the closest holes relative to source onto the holes situated further away. Again, at least one of the framing walls may comprise a panel, curved panel, tube or the like.

A particular embodiment is characterized in that at least one framing wall comprises a plurality of substantially axially arranged rings, each of which surrounds the detection chamber, as well as at least one framing wall which is substantially concentric with the rings and has at least one projection which extends at least partially parallel to a centre axis of the rings. In this embodiment, at least one framing wall is composed of rings, similar to, for example, the staves of a barrel. Of course an opening has been left between at least two rings. In addition, the embodiment comprises a framing wall with a projection which ensures that the basically annular gap between the rings is delimited to form a desired "net" opening in the framing wall. In addition, it is also possible for one or more, or all projections to be provided on one or more of the rings. In a preferred embodiment, the framing wall which is substantially concentric with the rings comprises a plurality of projections which are preferably placed at regular intervals. The projections preferably have the shape of a tooth, thus giving said framing wall the shape of a crown or crown wheel. Preferably, said projections extend over a number of the rings. With this embodiment, it is possible in a simple manner to change the dimensions of the "net" openings in at least one direction, in particular by making the distance between the rings adjustable.

Of course, in the abovementioned embodiment, it is also advantageous to make the rings and/or the one or more framing walls which are substantially concentric with the rings displaceable and/or rotatable or exchangeable. The advantages are similar to the advantages mentioned before and will not be repeated for the sake of brevity.

In a preferred embodiment, the pinhole wall comprises substantially a, preferably cylindrical or polygonal, pinhole wall with a plurality of pinholes around the detection chamber. Such a pinhole wall or pinhole tube preferably comprises a large number of pinholes, in particular between six and a thousand pinholes. Such a pinhole wall makes it possible to detect the detection chamber, and obviously makes it possible to detect in particular a test animal or test subject, at different angles. In this manner, it is possible to obtain a reliable three-dimensional image.

In a particular embodiment, the radiation detection device comprises a plurality of substantially concentric, and preferably cylindrical or polygonal, pinhole walls and/or a plurality of substantially concentric, and preferably cylindrical or polygonal, framing walls, each of which is removably positionable between the detection chamber and the at least one detector. This embodiment in particular, but not solely, provides advantages as a result of the fact that from the plurality of substantially concentric cylindrical pinhole walls, that pinhole wall can be selected which is most suited to the dimensions of the test animal to be examined or the individual to be examined. After all, it is expedient for the sensitivity of the radiation detection device if the pinholes are close to the test animal or the like. With the known devices, the dimensions of the pinhole wall were fixed, so that the known device could not be adjusted to the dimensions of the test animal or the part thereof to be examined. By now providing a radiation detection device with a number of pinhole walls, in each case one of which can be positioned around the detection chamber, the radiation detection device according to the invention is much more flexible in use. It should be noted here that with this embodiment the dimensions of the detection chamber may obviously vary. This embodiment may be provided as a system including a radiation detection device with a pinhole wall holder, as well as a case for the one or more other pinhole walls.

Preferably, the separate pinhole wall is displaceable and/or rotatable in the radiation detection device during a measurement. This creates the possibility of, for example, changing the beam paths and thus the image fields. For example, it is possible to turn a pinhole wall with pinholes in such a manner that the beam paths no longer appear to originate from a common centre, but rather seem to have a ring-like source. The central axis of each image field then comes from a direction which does not pass through the centre of the detection chamber. An advantage thereof is the fact that a relatively large part of the detection chamber can be imaged. In a particular embodiment, the at least one pinhole wall and the at least one framing wall are arranged so as to be displaceable, preferably rotatable, relative to one another in such a manner that the projection image fields on the at least one detector remain substantially in the same positions on the detectors during displacement, preferably rotation, of this at least one pinhole wall and this at least one framing wall. To this end, it is possible to provide a drive mechanism for said walls, in which the displacement, preferably the rotation, is coupled. For example, there is a fixed ratio between the displacement (speed) and change of angle (or angular speed) of the walls. It could be said that the projection image fields are not substantially changed, but the object image fields are, as in the latter case the viewing directions do indeed change. All this will be explained in more detail in the description of the figures.

In a particular embodiment, the radiation detection device according to the invention furthermore comprises an image-processing device which is designed to combine images from the detectors which were produced at different positions of at least one of the at least one pinhole wall and the at least one framing wall. In principle, it is of course possible to record individual images using the radiation detection device, at said different positions, and to process these images on an external image-processing device. For reasons of efficiency, it is advantageous to integrate the image-processing device with the radiation detection device, or at least to couple it with the latter. Such an image-processing device may for example comprise a computer with suitable software. The software preferably comprises image reconstruction software which can calculate an (original) image of an isotope distribution or the like of the test animal based on the images from the detectors. Preferably, in the case of images having overlapping image fields, the software is designed to use already calculated (parts of) isotope distributions at positions of the pinhole wall and framing wall in which the image fields do not overlap.

In particular, the image reconstruction may take place as follows. A source, such as a test animal, has a spatially extending isotope distribution A which can be divided into volume elements A(x,y,z), each of which contain an amount of isotopes. Using the radiation detection device, it is possible to carry out measurements, for example in a state of non-overlapping project image fields, all around, at different angles, the volume elements A(x,y,z) in each case being imaged on the detectors and there form image matrix elements B(x', y'), according to in each case a projection matrix P(n), it being possible for n to be a serial number, or a function of the angle setting, etc. The matrix elements of P(n) are known in each case, for example on the basis of calibration measurements. It is possible to derive the actual distribution A(x,y,z) from the total group of elements B(x', y') if certain requirements are met in respect of the angles at which measurements have taken place, etc. However, this applies to that part of the detection chamber where measurements could be carried out at those measurement angles. This is a central portion of the measuring chamber where the object image fields of the detectors overlap one another. It should be noted that if the test animal does not fit into the central portion in its entirety, there will thus be volume elements A(x,y,z) for which there are no or at least insufficient measurements to enable a correct reconstruction. It may nevertheless be advantageous to obtain information on this. The present invention makes this possible.

If, then, a switch is made to overlapping projection image fields, i.e. overlapping images B'(x',y') on the detectors, by suitable displacement of framing wall(s), etc., a different, for example larger, object image field will be created, at least for a number of detectors. In other words, information will become available, inter alia, for those extra elements A(x,y,z) which were previously outside the (object) measurement fields, together with information about previously known elements A(x,y,z) which can be obtained from B(x',y'). It could be said that a new projection matrix P'(n') is created. On the basis of P(n) and this new matrix P'(n') and the previously known information regarding A(x,y,z) in the central portion, it is also possible to solve the isotope distribution A(x,y,z) in the portion outside the abovementioned central portion in its entirety or at least partially.

The above reasoning applies both in the case where projection image fields are simply enlarged and in the case where the projection image fields are displaced in accordance with a displacement of the object image fields. In both cases, information becomes available on a portion of the detection chamber which could not previously be measured, but which can now be measured, at least partially, based on the known information.

In a second aspect, the present invention relates to a scintillation detection device, designed to detect high-energy radiation.

The invention also relates to a method for detecting high-energy radiation, in which such a scintillation detection device is used.

In particular, the second aspect of the invention relates to a scintillation detection device, designed for detecting high-energy radiation, and comprising a scintillation material for converting incident high-energy radiation into optical scintillation radiation, the scintillation material comprising a front side facing a source of the high-energy radiation, a rear side located opposite the former, as well as at least one lateral surface which connects the front side and the rear side, and a main detector located on the rear side of the scintillation material and designed for the position-sensitive detection of the scintillation radiation emitted by the rear side.

Such scintillation detection devices are well known in the prior art. The document NL-A-1021554, for example, describes a camera for radiation which comprises a position-sensitive light sensor and scintillation material.

One drawback of the known camera relates to the fact that the scintillation radiation to be detected is very weak. This is due to the fact, for example that the source may be a living animal or human, to which or to whom an amount of radioactive material has been administered. Obviously, the dose cannot be increased forever without causing damage. In addition, the scintillation radiation generated in the scintillation material by the incident high-energy radiation is emitted in all directions. The detector only collects a relatively small proportion thereof. Thus, it requires a relatively high administered dose before a sufficient number of detected events, i.e. scintillation flashes or interactions between the gamma quant and the scintillation material, are detected. It is therefore also important to detect as many events as possible as reliably as possible.

Another important criterion is the intensity or the amount of scintillation energy per event. The amount of scintillation energy is roughly proportional to the energy of the gamma quant. If the measured amount of scintillation energy is small, the uncertainty regarding the energy of the gamma quant is significant, and it is often not possible to ascertain whether it really is a gamma quant of known energy emitted by the source or whether it is something else, such as a cosmic ray or a gamma quant which has lost energy by scattering. Usually, it is preferable to avoid these last events.

Thus, one of the results of the fact that the sensitivity overall is relatively low is, inter alia, that the detected scintillation radiation may comprise a relatively large amount of noise, and has a relatively low energy resolution.

It is an object of the second aspect of the present invention to provide a scintillation detection device by means of which an improved energy resolution can be achieved.

This object is achieved according to the second aspect of the invention by a scintillation detection device, which is characterized in that the scintillation detection device furthermore comprises at least one lateral detector which is designed for detecting at least part of the scintillation radiation emitted by the lateral surface.

The purpose that the lateral detector serves is, at least partially, to detect scintillation radiation emitted by the lateral surface. In this way, a number of advantages can be achieved.

Thus, it can, for example, be determined more accurately whether the detected optical radiation indeed (directly) originates from high-energy radiation from the source, or whether it is a false-positive detection, for example triggered by cosmic radiation, or simply noise in the main detector. In addition, the resolution relating to the energy of the high-energy beam which caused the scintillation can be improved. The main detector, for example, collects 0.1% of the M generated scintillation photons of a single high-energy particle of, for example, 140 keV. If use is made of an optimally sensitive lateral detector, it is for example possible to collect as much as 10% of these M photons. This means that the absolute number of photons collected increases greatly, at least by the number of the photons additionally collected by the lateral detector, and thus the uncertainty relating to the energy of the high-energy particle is reduced. It should be noted here that the main detector of the scintillation detection device is position sensitive, which is often associated with a low absolute sensitivity. As the lateral detector does not have to be position sensitive, and may in principle occupy the entire surface of the lateral surface, the lateral detector can often have a much higher sensitivity than the main detector. This is used in an optimum manner by the scintillation detection device according to the invention.

In this application, high-energy radiation is understood to mean radiation which induces scintillation or fluorescence, in particular x-radiation and/or gamma radiation. Where the term "gamma" is used, for example in "a gamma quant" or "gamma radiation", this may always also comprise "an x-ray quant", "a scintillation- or fluorescence-inducing particle", etc. In this case fluorescence does not include the fluorescence used with neon tubes, and which is induced by UV radiation between 180 and 260 nm.

A particular embodiment comprises several lateral detectors arranged at mutually different positions around the lateral surface. In this manner, it is possible to gather information about the scintillation radiation emitted by the lateral surface in various directions. Such information may be useful when processing the scintillation radiation detected by the main detector. This will be explained in more detail below. Another advantage of providing several lateral detectors is that they can, if desired, be better attached to the lateral surface, as the lateral surface will be a substantially continuous surface, while the shape of the lateral detectors is often substantially straight.

In particular, the scintillation crystal comprises a substantially rectangular crystal, the lateral surface comprising at least one first and one second part surface, a first lateral detector of the plurality of lateral detectors being designed to detect the scintillation radiation emitted by the first part surface, and a second lateral detector of the plurality of lateral detectors being designed to detect the scintillation radiation emitted by the second part surface. In this embodiment, the crystal is rectangular, and thus has a lateral surface with substantially flat and straight part surfaces. The first and second lateral detectors can readily be attached to the latter. Incidentally, it should be noted here that in this document the term "crystal" refers not just to crystalline material, but in fact to any block of solid scintillation material, including amorphous material. By extension, it is also possible for liquid scintillation material to be provided in a container.

By means of the lateral detector, it is in addition possible to improve the signal-to-noise ratio of the main detector signal. In this case, use is made, for example, of the fact that the lateral detector will measure a stronger signal with an event which occurs at a position relatively close to the (part of the) lateral surface on which the lateral detector is located than with an event which is further away. Based on models or calibration measurements, it is thus possible to define a decision rule which for example determines in which half of the scintillation material the event took place, with this in many cases involving a half which is near the lateral detector and a half which is remote from the lateral detector. If it is found that an event took place, for example, in the first half, the main detector signal relating to measurements from the second half may be ignored, and vice versa. In this manner, the signal-to-noise ratio of the total main detector signal can be improved since possible noise signals from the detector half which is deemed to be irrelevant may be ignored. Other divisions and decision rules are likewise possible and may be selected on the basis of, for example, the positioning of the at least one lateral detector.

The positions of the first and second lateral detectors are not subject to any particular limitation. For example, the first and the second part surfaces are adjoining part surfaces. Thus, it is for example possible to obtain raw position information in two directions.

In a particular embodiment, the first and the second part surface are located opposite one another. In this manner, it is possible to determine the position much more accurately in the direction of a line from the first to the second part surface since now two amounts of scintillation energy can be compared, namely that which was measured by the first lateral detector and that which was measured by the second lateral detector. Thus, it is possible, to conclude that the event, that is the incidence of high-energy radiation which induced the scintillation, occurred, for example, at least approximately halfway between the first and second lateral surfaces. Using this information, it is possible to ignore, for example, part of the main detector signal. Particularly the signal relating to the measurement of radiation at positions which are remote from the event can be ignored. By removing such signals from the total measurement signal, the signal-to-noise ratio can be significantly improved. If the lateral detectors are very fast, it is in addition possible to use differences in the time at which an event is detected by the various lateral detectors in order to collect more detailed position information about the event. A further advantage is that reading out the detected information from the position-sensitive main detector can be limited to the selected areas, which may result in a time saving.

Preferably, the main detector is a two-dimensional detector. Obviously, this provides more spatial information regarding the distribution of the high-energy radiation, but this information can in addition be collected efficiently, as it is in this case simple to select only the relevant part of the detector. This is incidentally also possible if the main detector comprises a linear series of part detectors.

In a further particular embodiment, the scintillation detection device furthermore comprises a third and a fourth lateral detector, as well as a third and a fourth part surface, the third lateral detector being designed to detect scintillation radiation emitted by the third part surface, and the fourth lateral detector being designed to detect scintillation radiation emitted by the fourth part surface, the third and fourth part surface being located opposite one another. With this embodiment, position information about the event can be collected in two directions, substantially at right angles to one another. In this manner, the signal-to-noise ratio of the detected radiation can be improved still further. It should be noted that in this case a signal is considered to include, for example, a count of the number of events as a function of the detected energy, the energy in turn being determined from a number of photons associated with the event (the amount of measured scintillation energy). The technique of determining the position of the event from a measurement using the at least one lateral detector is also furthermore referred to as prelocalization further on in this document.

Another embodiment of the scintillation detection device is characterized in that it comprises at least one lateral detector with a plurality of partial lateral detectors. In this manner, it is possible to obtain still more accurate position information, as at least one part surface is divided further.

In particular, at least one lateral detector comprises at least one additional subdetector sensitive to scintillation radiation. In other words, the lateral detector itself directly measures the incident scintillation radiation using the subdetector. Such a subdetector may be, for example, a photodiode, a photomultiplier tube, etc.

In a particular embodiment, at least one lateral detector comprises an optical element which conducts the incident scintillation radiation to the subdetector. In this manner, the actual measurement thus takes place at some distance from the lateral surface. This may be convenient, for example if a specific other arrangement is desired, or for example a subdetector having a cooled housing, etc., is used. Examples of optical elements are a mirror, a prism, etc. which are all known per se to the person skilled in the art. In addition, the optical elements may perform additional functions, such as concentrating the radiation, in which case the optical elements comprise, for example, one or more lenses, or other bodies having one or more curved surfaces, such as granules, pills, and the like.

In a particular embodiment, the scintillation material comprises at least one bevelled edge on the side remote from the detector. The purpose of such an edge may be to reflect scintillation light in the direction of a part of the lateral detector which is sensitive to scintillation light. The bevelled edge comprises, for example, an edge at an angle of between 35 and 55, substantially approximately 45°, to the surface of the scintillation material, so that scintillation light emerging from the lateral surface is substantially reflected at a right angle. The latter obviously applies in particular if the scintillation material is (much) wider than it is thick, but nevertheless the bevelled edge will generally be able to direct the scintillation light efficiently onto the lateral detector. An important advantage is that the bevelled edge can very easily be provided on the scintillation material, for example by grinding down. If desired, the bevelled edge can be provided with a reflecting layer, for example a metal layer. It may for example be sufficient to bevel one single edge or even one single corner of the scintillation material in such a way, but combinations of edges and/or corners are also possible.

In a particular embodiment, the subdetector is integral with the main detector. In other words, the position-sensitive main detector additionally comprises a subdetector. In this case, the subdetector may be of the same type as the one or more part detectors making up the main detector, but this is not imperative. It may even be advantageous if the subdetector and the part detectors of the main detector are selected to be different, as they possibly have to meet different criteria.

In this case, it should again be noted that the scintillation detection device according to the invention can of course also comprise a plurality of subdetectors. The same is true for the main detector, which may optionally be integral with this plurality of subdetectors. Incidentally, it is still possible for the main detector and the one or more subdetectors to be physically separate units, but for the scintillation radiation which is emitted by the lateral surface to be conducted to the subdetector or subdetectors by means of an optical element.

In a particular embodiment, the optical element comprises at least one light guide which conducts the incident scintillation radiation to the subdetector. The significant advantage of a light guide is that once the light ray has been received in a conductive mode in the light guide, it can be conveyed over relatively great distances with, in principle, very little loss and it being possible to include various bends and the like. In this case, a light guide is understood to mean an elongate body made from optically transparent material with a substantially fixed cross section.

Furthermore, the invention provides an embodiment in which the main detector comprises a detector part which is sensitive to the optical radiation, as well as a series of light guides positioned between the rear side of the scintillation material and the detector part which is sensitive to optical radiation.

A very considerable advantage of the lateral detector in the scintillation detection device according to this embodiment relates to the sensitivity of a main detector which is coupled to the scintillation material by (a bundle) of light guides, which sensitivity is in itself relatively low. The advantage of the light conduction in the light guides, which advantage is used in order to significantly improve the position resolution, is detrimental to the sensitivity. After all, only a part of the scintillation radiation incident on an end face of the light guide can be received in the light guide in a conductive mode. In particular radiation which is incident at too great an angle to the longitudinal axis of the light guide is lost by attenuated reflection with the wall of the light guide. As a lateral detector does not need a light guide, in other words its sensitivity consequently does not decrease, great advantages can be achieved in respect of the energy resolution. Of course, prelocalization in this case offers the advantages already mentioned above as well. An example which may be mentioned here is that it is easy to provide a lateral detector which is, for example, ten times more sensitive than the combination of main detector and light guides.

In a particular embodiment, the light guide bundle comprises a bundle of light guides converging from the scintillation material to the main detector. With such a converging bundle of light guides, the position information at the location of the scintillation material is retained during conveyance thereof to the detector. However, the cross-sectional area of the bundle at the detector is smaller than at the scintillation material, as a result of which the detector can be made smaller as well, with all the ensuing advantages.

In particular, the main detector comprises a CCD or CMOS, but not exclusively. Using such devices as main detector expediently results in a position-sensitive high-resolution detector with a sufficiently high readout speed and sensitivity. However, other types of main detector are not excluded, such as arrangements of photodiodes and photomultipliers. It should be noted here that the at least one lateral detector may in principle comprise such a device, or a part thereof.

Such detectors for example offer the possibility to produce integrated measurements, so that for example the sensitivity can be increased. However, this also means that events which occur during the measurement time for an image or frame will coincide, so that for example two, three or more events will be detected in a frame. In general, it is possible that more event energy is detected in a frame than is appropriate for a single incident gamma quant. In order to resolve this energy information further, expedient use can be made of one or more lateral detectors.

In a further advantageous embodiment, the main detector and/or the lateral detector comprise/s a detector cooled to below ambient temperature, preferably a cooled CCD. Preferably, the scintillation material comprises scintillation material cooled to below ambient temperature. Such cooled components increase the sensitivity of the detection device. In particular, both parts (main/lateral detector and scintillation material) may be cooled using a liquefied gas, such as nitrogen. The detection device may to this end comprise a suitable container for coolant, or for example a Peltier element or other cooling device.

As has already been described above, the lateral detector does not have to be position sensitive. In a particular embodiment, the lateral detector does, however, comprise a position-sensitive detector. The lateral detector for example comprises several separate part detectors, such as for example a CCD which may or may not be separate, or a bundle of light guides which lead to a part of the position-sensitive main detector. A position-sensitive lateral detector offers the advantage that it is possible to obtain (more) position information on the depth of the event in the scintillation material. This may be important in order to determine the nature of the event, but may also be an additional way of checking if the event is genuine, particularly if at least two position-sensitive lateral detectors have been provided. After all, the depths determined by the at least two lateral detectors must correspond before an event is deemed to be genuine. Particularly advantageously, the scintillation material comprises several layers, for example layers of different material. Thus, a genuine event can be distinguished even better from a false-positive detection in, for example, a wrong layer. Also, knowledge about the layer in which the event occurred may be used to correct parallax errors, for example with pinhole gamma detection devices or with x-ray images. In particular if the scintillation material consists of different layers, each of which is optimized for a specific type of radiation or certain other conditions, the detector can be used for a wide variety of applications.

Advantageously, the at least one lateral detector is designed to carry out part measurements of the scintillation radiation with a lateral detection time for detecting which is at most half of the detection time of the main detector. Thus, it is possible to separate the actual events from false-positive measurements by applying a temporary window if the lateral detectors can measure more quickly than the main detector. The latter is relatively simple when the main detector is a CCD, for example with a frame measuring time of 50 Hz, at least for example between 1 and 1000 Hz. If then, for example, photodiodes are provided as lateral detectors, the lateral detectors for example are able to carry out measurements much more quickly, for example between 2 and 1000 times more quickly. The lateral detectors can divide each frame into at least 2, and for example between 2 and 1000 windows. If two or more lateral detectors simultaneously measure a flash, this is classified as a genuine event, while if only one lateral detector measures a flash, this is classified as noise, for example, at least the measurement or part measurement in question is ignored. Alternatively, a converted amount of energy can be subtracted from the main measurement.

It is also an important advantage that each event in a frame can be detected in a position-resolved manner by means of one or more quick lateral detectors. Consequently, it is not only possible to determine whether a flash is indeed an event, and not noise, for example when detections by two or more lateral detectors coincide temporally, but also where in a frame the event occurred. This makes it possible to determine very accurately whether a frame contains events, and if so, where in the frame these events took place. By then saving only those relevant portions of a frame and ignoring the remainder, the signal-to-noise ratio can be improved significantly by discarding false-positive detections. In other words, the use of lateral detectors offers the possibility of applying a spatial/temporal window to the detections, on the basis of which genuine events are distinguished from false-positive detections.

It is also possible to distinguish what are known as multi-photon events from events involving cosmic radiation of similar energy. After all, there will always be background noise caused by cosmic radiation, but with a very wide spectrum. An event caused by cosmic radiation with an energy which matches that of the source used cannot or cannot easily be distinguished from a genuine event caused by a gamma quant from this source. However, a frame with two or more events by gamma quants from this source can be distinguished from a single event caused by a cosmic quant having two or more times the energy of the gamma quants from the source used. After all, the events can be determined in a time-resolved manner to this end. Even without time resolution, a lateral detector is advantageous, as the energy resolution is improved with a lateral detector, as has already been explained above. Thus, even if the lateral detector is also a CCD or the like, and does not measure more quickly than the main detector, a multi-photon event can still be distinguished with a relatively high reliability as the signal-to-noise ratio for energy measurements is improved.

It is even possible to set the energy of an event if lateral detectors are fitted all around the scintillation material. Once the calibration measurements have been carried out, it is known how much energy will be collected by all the lateral detectors in total, at least within certain limits.

In a preferred embodiment, the scintillation detection device furthermore comprises a pinhole located at the front side of the scintillation material. Such an embodiment again offers the advantage of an increased potential sensitivity for the lateral detector, as the sensitivity of a pinhole detection device overall is already intrinsically low. After all, the radioactive source is viewed through a very small opening, the pinhole, so that only a very small part of the high-energy radiation emitted by the source reaches the scintillation material. In such cases, it is very important for the scintillation radiation generated by the small amount of high-energy radiation to be recognized as an event as reliably as possible. After all, if the number of events is low, often in a It should be noted here that the term "pinhole" ("hole") has the usual meaning of an opening permeable to high-energy radiation in a wall which is for the remainder substantially impermeable to this high-energy radiation.

Furthermore, it is possible for the scintillation detection device according to the invention to comprise a plurality of pinholes, such as a tube having a large number of pinholes. In that case, it is for example possible that a separate main detector is provided for each pinhole. It is also possible for several pinholes to cast an image onto a large main detector, the images preferably being separated from one another. To this end, a main detector of suitable dimensions can be provided, for example.

Furthermore, a scintillation detection device system can be provided, comprising a detection space and a plurality of scintillation detection devices according to the invention arranged around the detection space.

In a particular embodiment, the scintillation detection device comprises a data-processing device, the data-processing device being designed for processing detected scintillation radiation. In this embodiment, a data-processing device, in particular a computer, is coupled to the main detector(s) and the at least one lateral detector. This offers the advantage that the measurement signals, that is to say the detected scintillation radiation, can be processed in real time, so that additional measurements can be carried out, if desired. Of course, it is alternatively possible to only store the measured data and process these elsewhere, for example later, or to send them to a data-processing device via a network or another connection.

In particular, the data-processing device is designed to ignore the scintillation radiation detected by the main detector, if an amount of scintillation energy measured by at least one lateral detector of substantially simultaneously emitted scintillation radiation emitted by the lateral surface stays below a predetermined first threshold value, below a predetermined first threshold value and exceeds a predetermined second threshold value, or exceeds a predetermined second threshold value. A scintillation detection device according to this embodiment is designed for selecting suitable events, and consequently has a better signal-to-noise ratio. The threshold values can be determined from the scintillation to be expected on the basis of the kind of high-energy radiation which is being measured, the intrinsic sensitivity of the detection device, the dose of the radiation, etc. Calibration measurements are extremely suitable to achieve this. For example, undesirable kinds of events caused by cosmic radiation quants with an excessively high or excessively low energy can be filtered out.

In a particular embodiment, the data-processing device is designed for determining a position indication in the scintillation material of a source of the scintillation radiation with the aid of the at least one lateral detector. As has already been explained above, it is possible to obtain a position indication of the event resulting in this scintillation radiation on the basis of the scintillation radiation detected by the at least one lateral detector. On the basis thereof, the data-processing unit can then in turn determine which detection data from which part of the main detector should be used and which detection data from which other part should be ignored. This embodiment has an improved signal-to-noise ratio.

In particular, the data-processing device is designed for determining the number N of events in a measurement of the main detector, with the aid of the amount of scintillation energy detected by the at least one lateral detector or with the aid of the number of flashes in a specific energy range. If, for example, technetium with a particle energy of 140 keV is used as the radioactive source and if, with the aid of the at least one lateral detector, an amount of scintillation energy is determined which corresponds to for example a total particle energy of approximately 280 keV, then it can be deduced that in one detection or frame of the main detector, two events should be detectable, at least if both are the result of scintillation caused by the quant emitted by the technetium. The alternative, that is determining N using the number of flashes within a certain energy range, may be implemented by the lateral detector(s) carrying out several part measurements during a measurement by the main detector, in which a flash or event is only counted if the detected energy is within a predetermined range in order in this manner to exclude noise (usually too weak) or certain cosmic radiation (often too strong).

More in particular, the data-processing device is designed for determining N from the number of part measurements in which the amount of scintillation energy detected by the at least one lateral detector exceeds a predetermined threshold value or is between predetermined values. Since the main detector measurement can now be time-resolved by the at least one lateral detector, it is now also possible to look at the number of separate events within a total main measurement. After all, in principle any event in a separate part measurement can be determined by the at least one lateral detector. It should be noted that it is now possible to make a better distinction between several genuine events from the source used and false-positive detections on the basis of cosmic quants which coincidentally have two or more times the energy of the quants of the source. Obviously, it is advantageous in this case if the at least one lateral detector has a lateral detection time which is much less than the detection time of the main detector, advantageously at most 0.1× and more advantageously at most 0.01× the detection time of the main detector. If the main detector comprises a CCD or CMOS device, this is no problem at all for existing photodiodes, etc. On the basis of the detected, or at least suspected, number of genuine events, the genuine events can be determined more accurately in the image detected by the main detector, as a corresponding number of flashes can be selected in the image, and the other, in particular the relatively small flashes, can be ignored.

Perhaps superfluously, it is mentioned here that therefore the total energy detected in a frame or during a measurement by the main detector can be used to determine the number of events in that image, for example by dividing by the mean energy of a high-energy particle from the source used, which a measurement with the lateral detector(s) may support, which lateral detector may form part of the main detector. In addition, or even preferably, lateral detectors having a quicker detection time than the main detector are used, an event being recognized if two or more lateral detectors simultaneously detect scintillation radiation, during a measurement using the main detector.

On the basis of the detected number of events, these can be selected better and more accurately in frames/images of measurements by the main detector, so that parts thereof without events or even entire images in which no event appears to have occurred can be ignored. This reduces noise and increases the accuracy, so that it is moreover more readily possible to determine the focus of an event, as a result of which the resolution of the detection device again increases.

Preferably, the data-processing device is furthermore designed for determining a position indication for each of the N events in the scintillation material. It is then possible to obtain a position indication in the scintillation material for each separately determined event in the same manner as described above for a single event, so that on the basis thereof the radiation detected in the frame by the main detector can be selected more accurately and distinguished from noise. The above embodiments are thus also characterized by a very good signal-to-noise ratio, or at least by the possibility to distinguish a genuine signal (event) very accurately from noise and other false-positive detections.

In the second aspect, the invention generally also provides a method for detecting high-energy radiation, in which a scintillation detection device according to the second aspect of the invention is used. Use of such a scintillation detection device provides more information about the detected scintillation radiation, which information can be used in order to improve the signal-to-noise ratio, and thus for example also the position resolution and energy resolution of the scintillation detection device.

In particular, a method according to the invention comprises providing a radioactive source, detecting scintillation radiation emitted by the rear side using the main detector during a measurement time, as well as detecting scintillation radiation emitted by the lateral surface using the at least one lateral detector, in which an event in the scintillation radiation detected by the main detector is ignored if an amount of scintillation energy associated with that event and detected by the lateral detector stays below a predetermined first threshold value or exceeds a predetermined second threshold value. This is an elaboration on the method already referred to above in which only the correct events are selected for measurement, on the basis of the scintillation energy of the scintillation radiation detected by the lateral detector.

In a following particular embodiment, the method comprises determining an event in the scintillation radiation detected by the main detector, determining an amount of scintillation energy associated with that event using the at least one lateral detector, determining from the amount of scintillation energy from which part of the scintillation material the scintillation radiation originated; and narrowing the scintillation radiation associated with that event and detected by the main detector to scintillation radiation detected by a part of the main detector associated with that part of the scintillation material. This method is an elaboration on the method already referred to above in which only part of the scintillation radiation detected by the main detector is used, the part being selected on the basis of the position of the source of the scintillation radiation determined using the one or more lateral detectors.

Advantageously, the method comprises determining the number of events N in the scintillation energy detected by the main detector using the at least one lateral detector, and determining the N most likely separate events in the scintillation radiation detected by the main detector. As has already been described above, the number of events can be determined by either considering the total amount of scintillation radiation detected by the lateral detectors, which corresponds, for example, to 1, 2, . . . , N times the energy associated with a single incident high-energy quant, or by considering N part measurements in which in each case a separate scintillation by a quant from the source used is detected. Obviously, it will not be possible to prevent more events from taking place during a part measurement, but this is much less likely, especially with relatively very short lateral detection times, i.e. many part measurements.

In particular, the scintillation detection device comprises at least two lateral detectors, each having a lateral detection time for detecting the scintillation radiation which is at most half the measurement time of the main detector, each of the lateral detectors being designed for carrying out at least two part measurements during the measurement time, and the method ignores an event if at least two lateral detectors, and preferably all lateral detectors, detect a corresponding amount of scintillation energy in a corresponding part measurement. In this case, "a corresponding amount of scintillation energy" is understood to mean that the energy detected by the lateral detectors is associated with or could be associated with a genuine event. This may for example result in certain requirements being imposed on the minimum and/or maximum detected scintillation energy, as an energy which is too high or too low indicates a source other than a genuine event. In addition, it may result in requirements being imposed on the maximum ratio between the scintillation energy detected by the various lateral detectors, in dependence on the distance of the relevant lateral detector from the event. If only one, or at least not all lateral detectors detect scintillation energy during a certain part measurement, it is not a genuine event, but only noise or the like.

A general remark is made here regarding whether or not to ignore an event or whether or not to acknowledge an event as "genuine", and regarding the first and second threshold values. In some cases, it is important to actually select only the correct events, which makes it necessary to apply very stringent criteria, for example a narrow energy window between the first and second threshold value. This may mean that some genuine events will nevertheless be ignored, but does result in noise being reduced to a minimum. In other cases, amounts of energy which are as great as possible are the main concern, so that an isolated, noisy, false-positive event can slip through. The person skilled in the art is able to determine which strategy is most suitable.

In a third aspect, the present invention relates to a multiple image-forming device, comprising a first image-forming device and a second image-forming device connected to the former, as well as a support for an object to be examined, in which the first image-forming device comprises a radionuclide image-forming device with a first detection space, in which the second image-forming device comprises a Computer Tomography (CT) image-forming device with a second detection space, in which the support can be arranged displaceably in the first detection space and the second detection space.

Document U.S. Pat. No. 5,391,877 describes a combined CT-SPECT scanner, in which a computer tomography device and a SPECT scanner are arranged one behind the other, in such a way that a bed can be moved through both scanners. The images which are made by the CT scanner are used to determine the position in the images made by the SPECT scanner.

A drawback of this known device is that the CT scanner, which has to be screened against radiation, limits the accessibility of the detection space of the SPECT scanner. However, a SPECT scanner, or a radionuclide detection device in general, does not need to be screened at all, or at least far less. All this consequently results in the drawback that monitoring or working with an object on the bed during a radionuclide scan is rendered more difficult, while at the same time a CT scan is not always required. Modern radionuclide scanners in particular often offer a great depth because of the distance between an object and a detector, for example using pinholes positioned at different angles, etc. In addition, the screening which is not always required reinforces claustrophobia.

It is an object of the third aspect of the present invention to provide a combined image-forming device in which at least one of the abovementioned drawbacks has been eliminated at least partially.

The invention achieves this object in a third aspect by an image-forming device, in which the second image-forming device is displaceable relative to the first image-forming device between a first position and a second position, such that, in a first position, the first detection space and the second detection space adjoin one another and, in a second position, the first detection space is furthermore accessible from the side of the CT scanner via a path which is completely outside the second detection space. It should be noted that, in addition to the term scanner, the term image-forming device is used in this document, which is regarded as synonymous.

Making at least the CT scanner displaceable in such a way ensures that the accessibility of the detection space of the radionuclide scanner is only actually impeded when it is strictly necessary because a CT scan is required. If no CT scan is required, there is at least one other access path which does not pass through the CT scanning space, and which will therefore generally be shorter. Thus, a very user-friendly and flexible radiological image-forming device is provided. Not only is it often not necessary to carry out a CT scan in addition to a radionuclide scan, but it is moreover not always desirable to combine the CT scanner and the radionuclide scanner in one apparatus around one and the same detection chamber even if the possibility is provided. After all, one detector will always be arranged at least partially in front of the other detector, which may have adverse effects on the sensitivity, the resolution or also the complexity and the accessibility of components of the construction. According to the invention, with separate scanners and each having a scanning chamber, this is not a problem.

In this case, "adjoin one another" is understood to mean that there is a connecting path between the first and second detection spaces. Preferably, the smallest of the first and second detection spaces, over its entire cross section and at its connection to the largest of the first and second detection spaces, adjoins said largest detection space. More preferably, the first and second detection spaces are equally large in cross section.

In a particular embodiment, the first and the second detection space substantially do not overlap in the second position. In general, "substantially do not overlap" is in this context understood to mean that the projection in the direction of the support of the (cross sections of the) smallest of the two detection spaces is at least partially outside that of the largest detection space. In this case, "not overlap" refers in particular to the situation where the projections in the direction of the support of the (cross sections of the) detection spaces do not overlap at all, in which situation the accessibility of the first detection space is increased in an optimum manner on that side.

In a particular embodiment, the radionuclide scanner, at least on the side facing the CT scanner, comprises an access space to the first detection space, which access space is tapered, in particular frustoconical, the second detection space and the access space substantially not overlapping in the second position. Such an embodiment is expedient if the radionuclide scanner comprises, for example, a plurality of pinholes, which form images of the object to be examined at different angles. The access space then often has the shape described, which then has a larger cross section than the actual first detection space. The fact that this access space is made freely accessible as far as possible and substantially completely is a significant advantage of the image-forming device according to the invention, as the working space is thus greatly increased.

Advantageously, the CT image-forming device comprises a portion which surrounds the second detection space in said plane, the portion comprising a first part and a second part, the first part being displaceable along a movement path which is at an angle to the direction of the support, at least locally. As a result, the "ring" around the CT detection space can be split, it being possible to move at least one portion, but for example also two portions, away in order thus to open the first detection space completely or partially.

In particular, the first part comprises a body with an opening which extends partially in annular fashion around the second detection space, the second part filling the opening in the first position and, together with the first part, forming a complete ring around the second detection space, and the opening, perpendicular to the direction of the support, having a width which is greater than the width of the support. Such an embodiment also makes it possible to move the largest portion of the CT scanner away from the support if the support is located in the second detection space. Said first part can then move "over the support" via the opening, which offers the possibility to decide even during a scan whether to include or exclude the CT image-forming device. Thus, the possibility is offered, for example, to continue a radionuclide scan even if the CT scan had to be interrupted due to panic or for other reasons. Incidentally, with this embodiment, the x-ray source and detector(s) can still describe a path around the support. The source and the detector are for example connected to one another by a semicircular frame, and thus could each cross the opening. Alternatively, a guide and/or drive is provided in the first and in the second part, the guides and/or drives of the two parts adjoining one another in the first position.

In one embodiment, the support comprises a substantially vertical support rod and a support base, relative to which the support rod can be displaced in at least one direction, and the CT image-forming device can be guidably displaced over the support base in the direction of the support, and the multiple image-forming device comprises a radiation screening cover which can be attached to the radionuclide image-forming device. Preferably, the radiation screening cover and a housing of the radionuclide image-forming device in the first position thus form a substantially continuous entity. In addition to the fact that the support base is used, which is present already and often is a table, it is an advantage of this embodiment that the combination can be of a rather compact design in order to support the CT scanner. After all, the support does not have to be able to be displaced through the radionuclide image-forming device (RNBI) as far as into a CT scanner arranged behind the latter, which would result in a very long support due to the often much more voluminous RNBI. The latter is disadvantageous with regard to the stability and reproducibility of measurements.

Preferably, the radiation screening cover consists of several parts which can slide over one another, for example telescopically. Thus, it is possible to provide a very compact multifunctional image-forming device, which makes optimum use of the fact that a CT scanner is often much less wide than an RNBI, and which can also easily be used when space is at a premium. In this case, for example, one cover part may be fixedly arranged relative to the support and another cover part may be fixedly arranged relative to the CT scanner. Alternatively, one or more cover parts can be displaced independently.

In one embodiment, the first part comprises a body extending in a plane all around the detection space. In this case, the first part forms a continuous body, or ring, which is displaced in its entirety. This offers advantages with respect to the x-ray source and detector, which can often be moved around the detection space and can now freely rotate around the latter.

In a preferred embodiment, the movement path comprises a line at a preferably right angle to the direction of the support. Thus, the first part, and optionally, if the case arises, the second part, can be displaced in a straight line in order to give access to the first detection space, at least partially. This offers the advantage that a minimum space requirement, that is surface area requirement, is necessary for the total image-forming device. Preferably, the line is a vertical line, as the vertical space is often not a limiting factor in a building space and as this space is often unused. Obviously, the line may also be an inclined or even horizontal line. In addition, as an alternative, it is also possible to design the movement path as a curve, along which the first part is displaced. Furthermore, the second part may be displaceable along its own, different movement path. Examples of such curves are a part of a circular arch, if the first part is rotated about an axis, or combined lines and circular arches, such as a partly straight displacement followed by a tilting about an axis. All this depends on the space requirement the total image-forming device is allowed to have. It should be noted that curves will be locally straight, i.e. will have a tangent. The local tangent will then form the relevant angle with the direction of the support.

In a particular embodiment, the support is displaceable relative to the first detection space in a direction at right angles to the direction of the support. In this manner, it is possible to scan a larger part of the individual, animal or object on the support. This is mainly to do with the fact that particularly radiological scanners using pinholes often cannot scan the first detection space completely, i.e. not simultaneously using all pinholes. Usually, there is only a central section of the first detection space which is scanned by (virtually) all pinholes, or at least to a sufficient degree to be able to perform a sufficiently reliable image reconstruction. By now displacing the support according to the measure, in each case a different part of the object or individual 20 can be placed in that central portion. Incidentally, in principle this principle also applies to the CT scanner.

The aspects of the invention will be explained in more detail below with reference to the drawing, in which some non-limiting embodiments are shown and described and in which:

FIG. 1 diagrammatically shows a cross section (not to scale) through a radiation detection device according to a first aspect of the invention;

FIG. 2 shows a longitudinal section (not to scale) through another embodiment of the radiation detection device according to a first aspect of the invention;

FIG. 3 diagrammatically shows a side view of a scintillation detection device according to a second aspect of the invention;

Figures 9A, 9B:
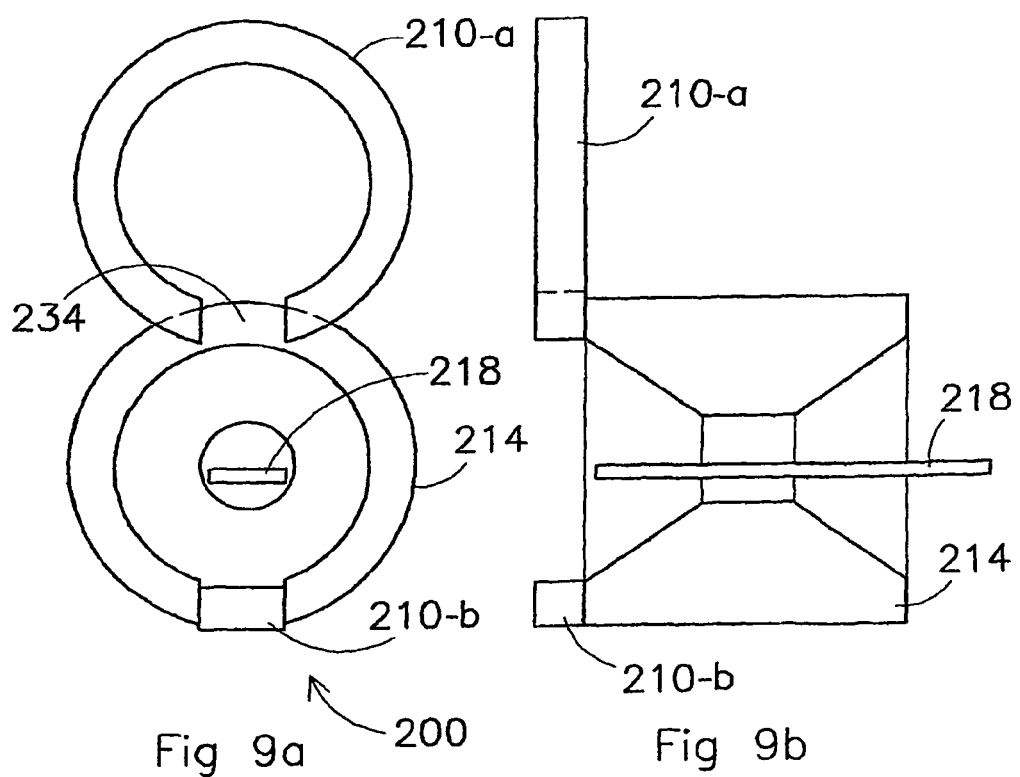
Figure 10:
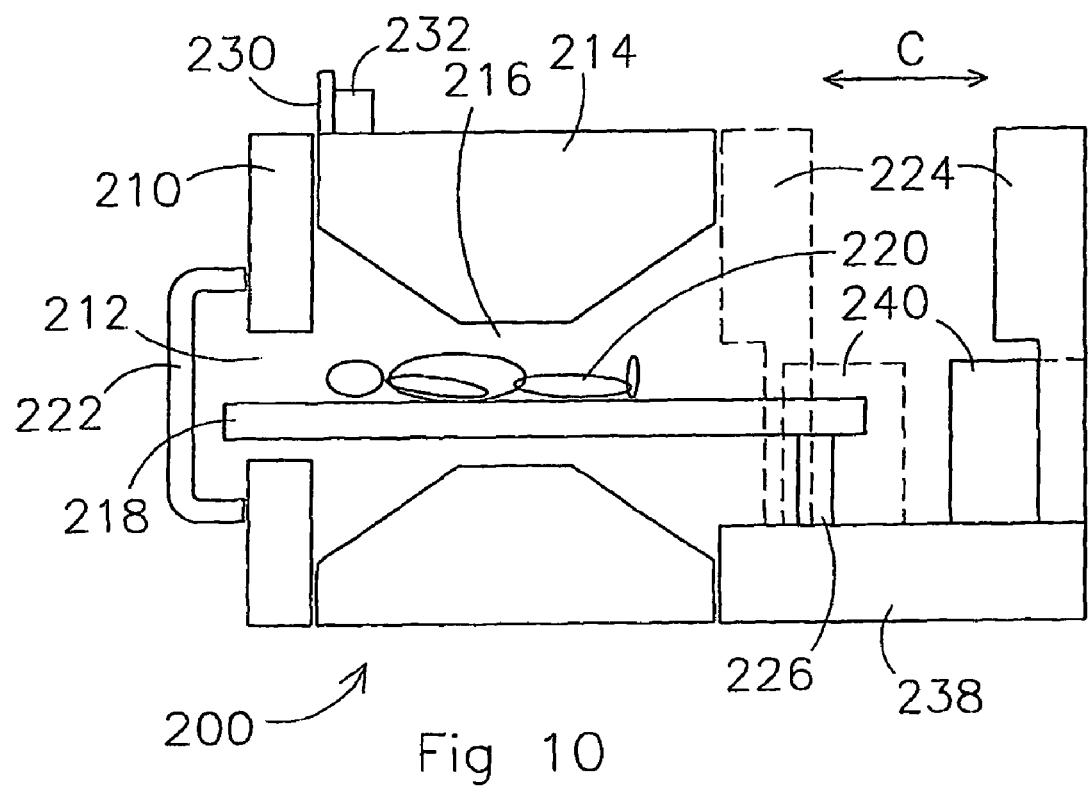

FIGS. 8a and 8b diagrammatically show a first embodiment of a scanner 200 according to a third aspect of the invention;

FIGS. 9a and 9b show a diagrammatic front and side view, respectively, of an embodiment of the multiple image-forming device according to a third aspect of the invention; and FIG. 10 shows a diagrammatic side view of another embodiment of the multiple detection device according to a third aspect of the invention.

Figure 1:
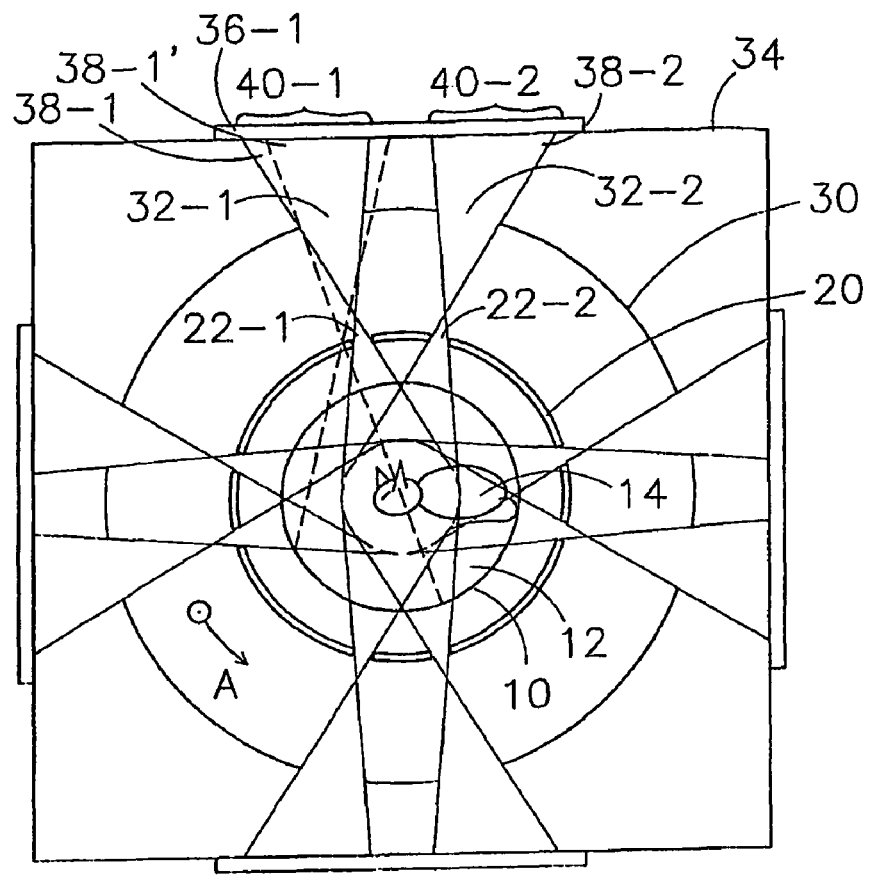

FIG. 1 diagrammatically shows (not to scale) a cross section through a radiation detection device according to a first aspect of the invention. In this case, the radiation detection device, generally denoted by reference numeral 1, comprises an inner tube 10 which delimits a detection chamber 12, in which a test animal 14 is located.

This is surrounded by a pinhole wall 20 with, in this case, 8 pinholes: 22-1, 22-2, 22-3, 22-4, 22-5, 22-6, 22-7, 22-8. This is enclosed by a framing wall 30 having 8 openings: 32-1, 32-2, . . . . Around this, as the outermost component illustrated, there is a detector wall 34 having four detectors 36-1, . . . .

Each of the pinholes 22-1, 22-2, . . . , has a field of vision 38-1, 38-2, . . . , which is bounded by the openings 32-1, 32-2, . . . , and which casts an image field 40-1, 40-2, . . . onto the detector 36-1, . . . .

At least one of the pinhole wall 20 and the framing wall 30 is displaceable in the direction of the arrow A and/or in a direction at right angles to the plane of the figure.

The inner tube 10 is optional, as the detection chamber 12 may also be formed by the chamber which is delimited by the pinhole wall 20. However, the inner tube 10 often is a structure in which the test animal 14 is situated. Incidentally, the shape of the tube 10 is not limited to a cylinder, but can also be box-shaped, etc. The cross section of such a tube, cylinder, etc., is not subject to any particular limitation. In a practical example, this is for example 44 mm for a mouse and 100 mm for a rat. In case the tube can be moved with respect to the pinholes, a smaller cross section may be selected, such as 35 mm for the mouse and 70 mm for the rat, and 600-800 mm for a human head. Both the sensitivity and the resolution increase when the achievable distance between the test animal and the detector is reduced, which is one of the advantages of the invention.

In FIG. 1, the pinhole wall 20 comprises eight pinholes or openings in a wall which, for the remainder, is substantially impermeable to high-energy radiation. A different number of pinholes may also be chosen, for example 2, 3, etc. In particular, the pinhole wall 20 overall comprises many pinholes, such as 75 or even more pinholes. In this manner, it is possible to obtain images of the test animal 14 at many different angles without the test animal 14 having to be moved or the like. This provides a reliable three-dimensional image of the test animal, at least of the distribution of radioactive material in the latter. After all, one single pinhole does not yield any depth information; this can only be obtained by combination with other pinhole images.

The pinhole wall 20 may be made from any suitable material. As the thickness of the pinhole wall 20 is in principle not subject to any particular limit, very many materials may be taken into consideration, such as steel, tungsten, etc. The pinholes 22-1, 22-2, . . . , comprise small, substantially round openings having a cross section of for example a few tenths of millimetres, such as 0.6 millimetres, and the area directly surrounding the opening itself is preferably made of a material which has a very high capacity of blocking the high-energy radiation. Examples of such materials are lead, tungsten, (depleted) uranium and, for example, gold.

The field of vision of a pinhole 22-1, 22-2, . . . , also expressed in the form of an aperture angle, is often relatively large, around 30 degrees, for example. In addition, due to the round opening, the resulting field of vision is also round. However, the detectors which are used most often are substantially rectangular. In addition, ordering the image fields 40-1, 40-2, . . . of the pinholes is more efficient if the resulting image fields are rectangular. It is, inter alia, for the above-mentioned reasons that the framing wall 30 is provided, with openings 32-1, 32-2, . . . as a result of which the respective fields of vision 38-1, 38-2, . . . are bounded and rectangular image fields 40-1, 40-2, . . . which in this embodiment substantially do not overlap are produced.

According to the invention, at least one of the pinhole wall 20 and the framing wall 30 can be displaced such that at least one of the image fields 40-1, 40-2 can be changed in size and/or direction. In the embodiment shown in the figure, the pinhole wall 20 can, for example, be rotated about its centre axis, in the direction of the arrow A, or opposite thereto. If the framing wall 30 does not move along with it, the following change will take place in the central image field, indicated by the central dotted line in the detection chamber 12. In the fields of view 38-1, 38-2, . . . indicated by full lines in FIG. 1, a central part of the detection chamber 12 which is imaged by all pinholes 22-1, 22-2, . . . is shown. If the pinhole wall 20 is rotated in the direction of arrow A, the field of view 38-1, for example, changes into the new field of view 38-1, which is delimited by two drawn dotted lines. A correspondingly shifted image field on the detector 36-1 is not illustrated separately. It can clearly be seen that the portion of the detection chamber 12 which can be observed shifts. A similar shift will occur in the case of the other seven pinholes 22-2, . . . , as a result of which a much larger section of the detection chamber 12 can be observed, albeit with a loss of spatial information per volume element, as not all pinholes can obtain a complete image of each volume element. Nevertheless, valuable information can be obtained about the surrounding area of the central portion of the detection chamber 12.

Alternatively, instead of the pinhole wall, the framing wall can be displaced, for example rotated in the direction of the arrow A. In that case, a similar change and/or shift of the respective fields of vision 38-1, etc. may occur. It is also possible to displace both the pinhole wall 20 and the framing wall 30, preferably by means of a coupled displacement. Thus, it is for example possible to rotate both the pinhole wall 20 and the framing wall 30 at an identical angle in the direction of the arrow A. In that case, the field of vision will not change shape, but it will change direction, whereas the image field, which is a projection of the field of vision on the detector, may change. From a mathematical point of view, this can be compared to rotating the test animal 14 in the detection chamber 12. On the other hand, this may not be possible, for example because the test animal 14 might move, such as on account of the force of gravity. This would result in a change in shape of the test animal 14 or a part thereof to be examined, which is undesirable.

The illustrated detector 36-1 may for example comprise an arrangement of light-sensitive elements, such as photodiodes. Alternatively, the detector 36-1 may comprise one or more CCDs or CMOS devices. Such devices can nowadays be produced on a relatively large scale and with relatively large dimensions, while offering a very good resolution.

Figure 2:
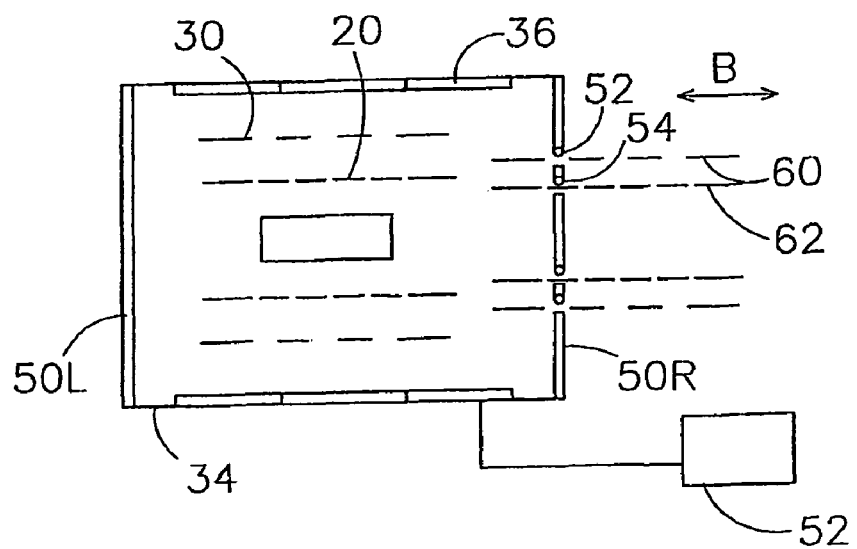

FIG. 2 shows (not to scale) a longitudinal section through another embodiment of the radiation detection device according to a first aspect of the invention. In this figure, as in the entire drawing, identical components are denoted by the same reference numerals.

Detection chamber 12 is surrounded by a pinhole wall 20, a framing wall 30 and an outer wall 34 with detectors 36.

50L and 50R are a left-hand and right-hand radiation screen, respectively. 52 and 54 are a first motor and a second motor, respectively, for a second framing wall 60 and a second pinhole wall 72, respectively. Reference numeral 52 indicates a data-processing device.

In the illustrated embodiment, the detection chamber 12, for example, can be moved in the direction of the arrow B. In particular, this detection chamber 12, more precisely the wall around this detection chamber 12, can be replaced through displacement by another wall, in particular another wall of different dimensions. Thus, it is possible to provide a detection chamber which is adapted in an optimum manner to the dimensions of the object, test animal or individual to be examined.

In a similar manner, a second pinhole wall 62 is provided, having different dimensions, in particular a different cross section. Thus it is possible to select a pinhole wall which is adapted in an optimum manner to the dimensions of the object, test animal or individual to be examined. In practice, the pinhole wall 20 will be extended by means of a motor (not shown) when the pinhole wall 62 is retracted by means of the second motor 54. Alternatively, the various motors may be omitted and replaced by a guide rail, an adjusting screw, etc. All this may also take place during one and the same measurement, and consequently it is for example possible to make a plurality of images using different pinhole walls 20, 62, etc. of the same test animal.

Similarly, in the illustrated embodiment, the framing wall 30 may be replaced or supplemented by a second framing wall 60, for example by means of a first motor 52. By retracting the second framing wall 60, if desired only partly, the "net" image fields on the detectors 36 can be changed, in which case it is relevant that the part of the detection chamber 12 which is imaged is changed accordingly as a result. It should be noted that the openings in the framing walls 30 and 60 can interact, in order to form the "net" openings. Alternatively, it is possible to opt for arranging only one framing wall, by retracting one framing wall and extending the other one. It should be noted here that, alternatively or additionally, the framing wall(s) can be placed between the source 12 and the pinhole wall(s).

Of course, said measures, i.e. displacing the detection chamber, the pinhole wall(s) and framing wall(s), may be combined as well as optionally supplemented by rotations thereof about a centre axis. In addition, in this case only two pinhole walls 20, 62 and two framing walls 30, 60 are illustrated. Of course, it is possible to provide a plurality of framing walls and pinhole walls, as well as a plurality of detection chambers.

In this case, a total of 6 detectors 36 are shown, this number obviously not being limiting in any way. The detectors 36 can, for example, be read out, and the read-out data can be processed with the aid of a connected data-processing device 52. This will usually be a computer with suitable software. Alternatively, it is possible to process the read-out data separately later.

Figure 3:
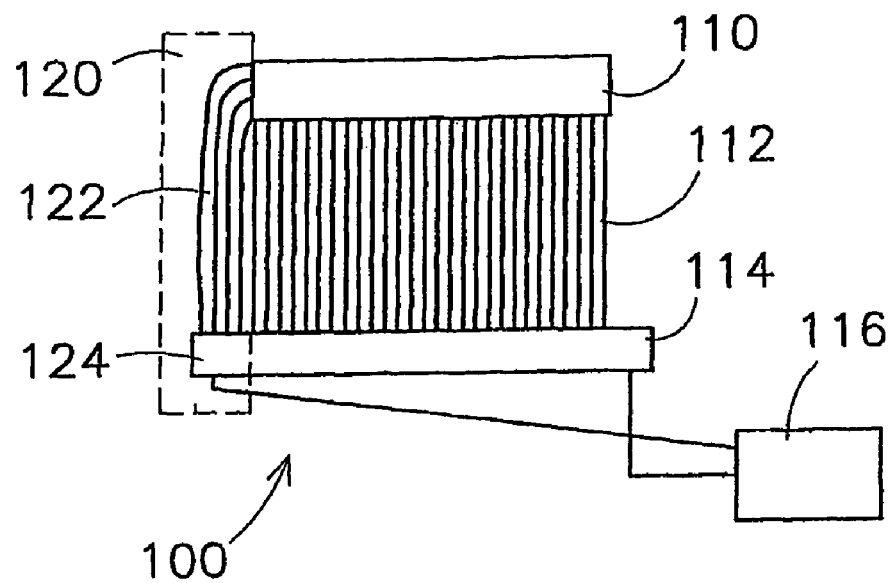

FIG. 3 diagrammatically shows a side view of a scintillation detection device according to a second aspect of the invention. The scintillation detection device 100 comprises scintillation material 110, a bundle of light guides 112, a main detector 114, an optional data-processing device 116 and a lateral detector 120.

The lateral detector 120 also comprises a bundle of light guides 122 as well as a subdetector 124.

The scintillation detection device shown in FIG. 3 is a simple example and, for example, works as follows. Incident high-energy radiation causes scintillation in scintillation material 110. The scintillation radiation generated will partly end up in the bundle of light guides 112, which transmit the scintillation radiation and the position information contained therein to the main detector 114. This is, for example, a CCD or the like. The CCD is read out by data-processing device 116, for example a computer. The computer 116 can subsequently start to process the read-out information.

The lateral detector 120, which is indicated by the dotted line, is designed to collect scintillation radiation emitted by a lateral surface of the scintillation material 110. This radiation is conducted to the subdetector 124 via a bundle of light guides 122. The bundle of light guides 122 may in principle be a bundle of light guides similar to those of the bundle 112, but may particularly differ by the fact that the numerical aperture of the light guides 122 is chosen to be as large as possible. After all, one of the main functions of the bundle of light guides 122 is to collect light in an absolute sense, without the necessity for any position resolution. In fact, the bundle of light guides 122 could equally well be a single light guide.

The subdetector 124 is in this case integral with the main detector 114. The subdetector comprises unused pixels of the CCD 114, for example. Alternatively, the detector 124 may also be a separate light-sensitive sensor, such as a single photodiode or the like. Subdetector 124 is also connected to computer 116.

Figure 4A:
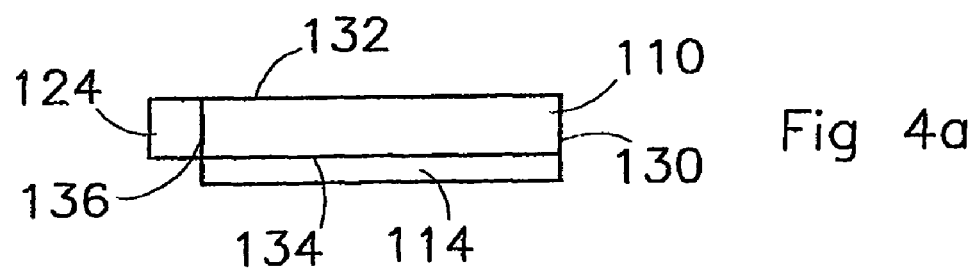
FIGS. 4a, 4b and 4c show alternative embodiments of the scintillation detection device in diagrammatic side view.
Figure 4B:
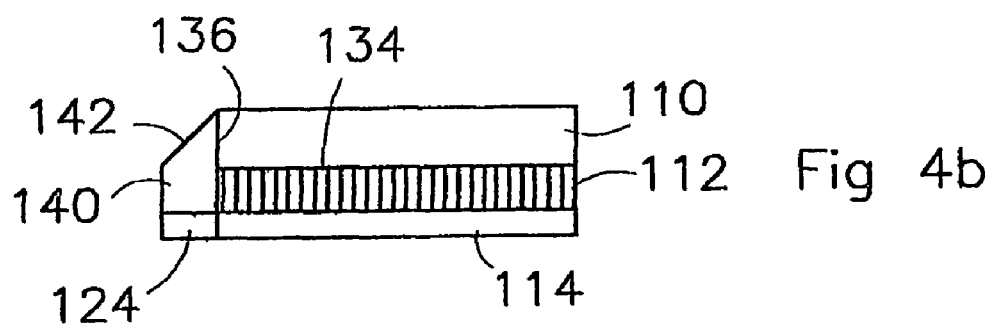
Figure 4C:
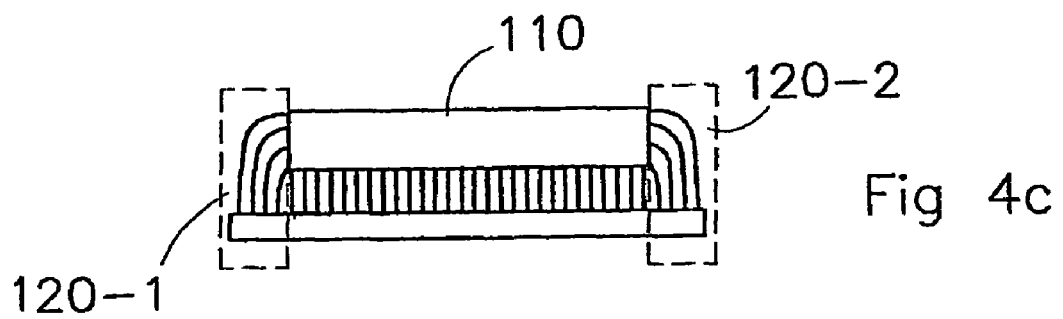

FIGS. 4a, 4b and 4c show alternative embodiments of the scintillation detection device, in diagrammatic side view. In these figures, as in the entire drawing, identical components are indicated by the same reference numerals.

In FIG. 4a, an embodiment comprises scintillation material 110, having a top side 132, a first part surface 130, a bottom side 134, and a second part surface 136. On the bottom side 134, a main detector 114 is arranged, while on the second part surface 36, a subdetector 124 is arranged.

In this minimal embodiment, both the main detector 114 and the subdetector 124, which effectively forms the entire lateral detector, are arranged directly on the scintillation material. Thus, the least scintillation radiation will be lost in components between the scintillation material and the respective detectors.

The subdetector 124 is arranged over the entire width, even over the entire surface of the second part surface 136, so that as much as possible of the scintillation light emerging from that second part surface is collected.

In the embodiment according to FIG. 4b, a bundle of light guides 112 furthermore connected to the main detector 114 is provided on the bottom side 134.

An optical element 140 with a reflecting surface 142 adjoins the second part surface 136.

In this embodiment, the lateral detector is formed by the optical element 140, and the subdetector 124. The scintillation light emerging from the second part surface 136 will be conducted to the subdetector 124 by the optical element 140 via the reflecting surface 142, at least to a large extent. To this end, the optical element 140 comprises an optically transparent material, such as glass, quartz or the like. The reflecting surface 142 may be designed as a surface of a prism, i.e. at for example 45° and using completely internal reflection, but this depends on the average exit angle of the scintillation light. This measure usually suffices when the thickness/length ratio of the scintillation material 110 is small. Alternatively, the reflecting surface 142 may for example also be designed as a mirror. Particularly scintillation radiation which is generated close to the second part surface 136 can thus be better reflected in the direction of the subdetector 124.

The subdetector 124 may in this case again be an integral part of the main detector 114, such as a number of pixels of a CCD. However, subdetector 124 may be a separate photosensitive detector, such as a photodiode or photomultiplier, in this case as well.

FIG. 4c shows a different embodiment which comprises two lateral detectors 120-1 and 120-2. The structure of the lateral detectors 120-1 and 120-2 in each case corresponds to the structure according to FIG. 3 and will therefore not be explained in any more detail. An advantage of the embodiment according to FIG. 4c is that the position of an event, that is to say the source of the scintillation radiation in the scintillation material 110, can be determined relatively accurately. To this end, the scintillation light measured by the lateral detector 120-1 can be compared to the amount of scintillation energy measured by the lateral detector 120-2. On the basis of the ratio between the measured amounts of light, the position between the two lateral detectors 120-1 and 120-2 can be determined, at least at surface level.

Figure 5A:
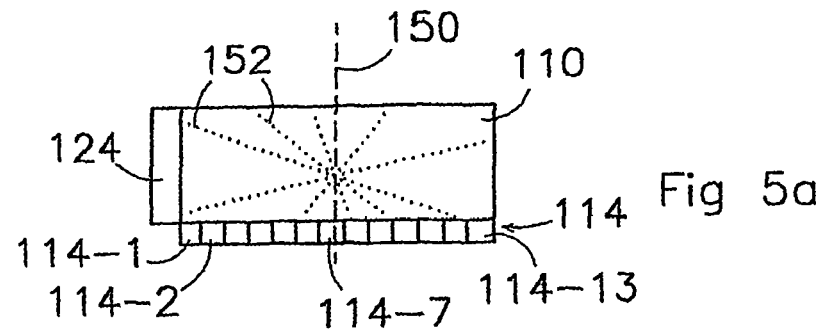
FIGS. 5a, 5b and 5c show an application of the lateral detector at the prelocalization of an event.
Figure 5B:
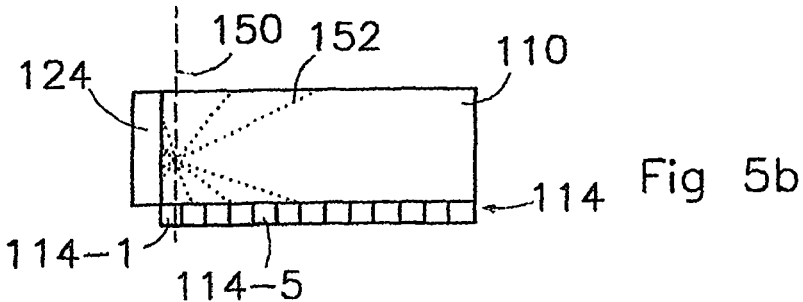
Figure 5C:
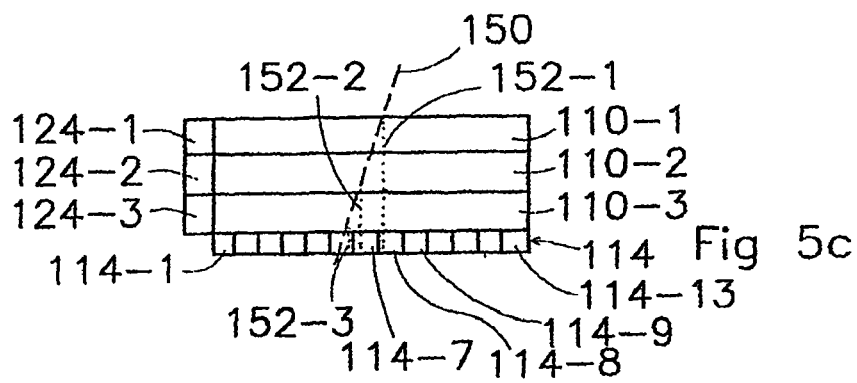

FIGS. 5a, 5b and 5c show an application of the lateral detector at the prelocalization of an event.

In this case, 150 is an incident gamma quant, which generates scintillation photons 152 at a certain depth in the scintillation material. A lateral detector or subdetector is denoted by 124, and a main detector by 114, which is subdivided into thirteen part detectors 114-1 to 114-13.

As can be seen, the incident gamma quant 150 reacts to the scintillation material 110, and generates optical scintillation radiation in that material. For the sake of convenience, this is shown by ten photons 152, whose "path" of later interaction or detection is illustrated by means of dotted lines. Such scintillation radiation is in principle distributed arbitrarily, and in the figure, five photons go to the left and five go to the right.

In FIG. 5a, the gamma quant enters the scintillation material 110 approximately in the centre. At a certain depth, the interaction, also referred to as the event or the flash, takes place. A certain part of the scintillation radiation reaches the subdetector 124, and a certain part also reaches one or more part detectors, which are on average close to the part detector, through which the line of the propagation direction of the gamma quant also goes or would go, in this case part detector 114-7.

According to a predetermined rule, on the basis of for example calibration measurements, it is possible to determine from the number of scintillation photons collected, in this case 2, that the event occurred approximately in the centre of the detector 114. On the basis thereof, detections by part detectors which are remote from the centre can be ignored, for example by setting or programming an image-processing device accordingly (not shown). For example, detectors 114-1 to 114-4 and 114-9 to 114-13 could be ignored, so that any noise from those detectors can also be ignored. Other divisions are possible as well.

In FIG. 5b, the gamma quant lands on the far left, along a line which goes through the part detector 114-1. Because of the small distance, all five scintillation photons 152 which move to the left of the total number of ten scintillation photons 152 impinge on the subdetector 124. On the basis of this strong(est possible) signal, the decision may be taken to use, for example, part detectors 114-1 to 114-5 and to ignore the others.

If a second subdetector 124 is to be provided on the opposite side of the scintillation material 110 too, it is possible to determine a position of incidence of the gamma quant on the basis of the differences in the measured amount of scintillation energy. This so-called prelocalization can then be carried out even more accurately than in the case where only one subdetector 124 is used.

All this will be explained in more detail in FIG. 6

FIG. 5c again shows a diagrammatic cross-sectional view of an embodiment. The scintillation material now comprises three layers 110-1, 110-2 and 110-3 made of identical or different material. Furthermore, the lateral detector 124 comprises three subdetectors 124-1, 124-2 and 124-3.

Again, 150 denotes a gamma quant. Furthermore, three dotted lines 152-1, 152-2 and 152-3 diagrammatically indicate where the focus of the scintillation radiation would be detected if the interaction were to take place in layer 110-1, 110-2 or 110-3, respectively.

It can be seen that the scintillation detection device may suffer from a parallax error, if it is not exactly known at which depth a gamma quant which is not incident at right angles interacts with the scintillation material. After all, an event which occurs in layer 110-1 will mainly be detected by part detector 114-9 of the main detector 114, while an event which occurs in layer 110-2 or 110-3 will mainly be detected by part detector 114-8 and 114-7, respectively. In other words, the detection location depends on the depth at which the event occurs, while in fact exactly a detection location which corresponds to the intersection of the propagation direction of the gamma quant and the detector 114 would have to be detected. This is also referred to as the depth-of-interaction problem.

In the detection device illustrated, use may be made of position-sensitive lateral detectors 124-1 to 124-3. After all, an event occurring in layer 110-1 will mainly, that is to say most strongly, be detected by the subdetector 124-1, while an event occurring in layer 110-2 or 110-3 will mainly be detected by subdetector 124-2 and 124-3, respectively. By now determining which subdetector measures the strongest signal, it is possible to determine in which layer the event occurred, and if desired the detected position can be corrected for the angle of incidence. The latter can be determined, for example, from the detected position of the event and the position of, for example, the pinhole from which the quant came. Other corrective measures are also possible. The example using a three-layer scintillation material is of course not limiting, and it is also possible to provide two, or four or more layers. The lateral detector may also comprise a different number of subdetectors, but preferably at least one subdetector per layer of scintillation material, and more preferably several subdetectors per layer of scintillation material. It is also possible to reduce the depth-of-interaction problem with a single-layer scintillation material if the lateral detector comprises several subdetectors, or is at least position sensitive. It should be noted that a lateral detector which is not position sensitive, with or without a single-layer scintillation material, cannot make the abovementioned distinction.

Figure 6:
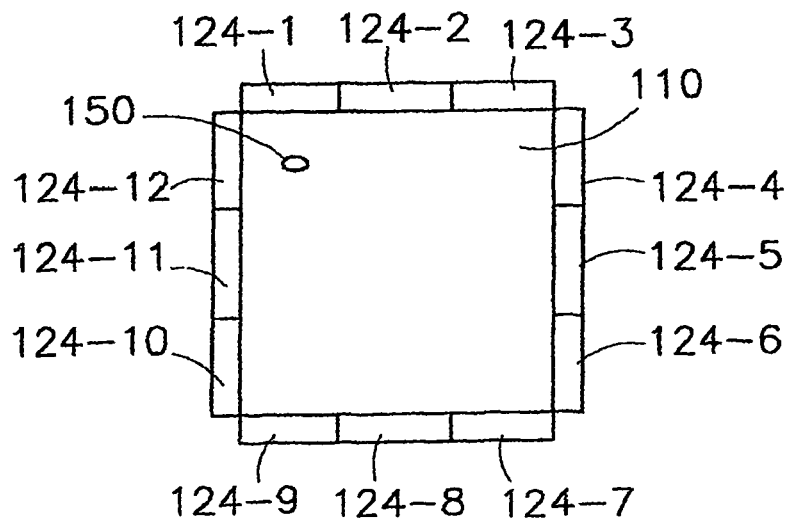
FIG. 6 shows a top view of a different embodiment.

FIG. 6 shows a top view of another embodiment.

In this embodiment, 110 again denotes scintillation material on which a gamma quant 150 lands at the position of the circle, which scintillation material is surrounded by twelve subdetectors 124-1 to 124-12.

It will be clear that subdetectors 124-1 and 124-12 will measure a stronger signal than, for example, 124-9 and 124-4, respectively, but effectively also stronger than any other subdetector. On the basis thereof, it is possible to determine that the event occurred at "coordinates" (124-1, 124-12). In a similar manner, the scintillation material may be divided into, in this case, nine sections, but obviously other numbers are also possible, thus making substantial prelocalization possible. Incidentally, it is assumed in this case that the angle of incidence of the gamma quants is relatively large, which can be achieved in a suitable manner by suitable screening on the entry side. If the latter has not been arranged, an accordingly larger share of the part detectors may be involved in the final measurement in order to a take this into account.

Figure 7:
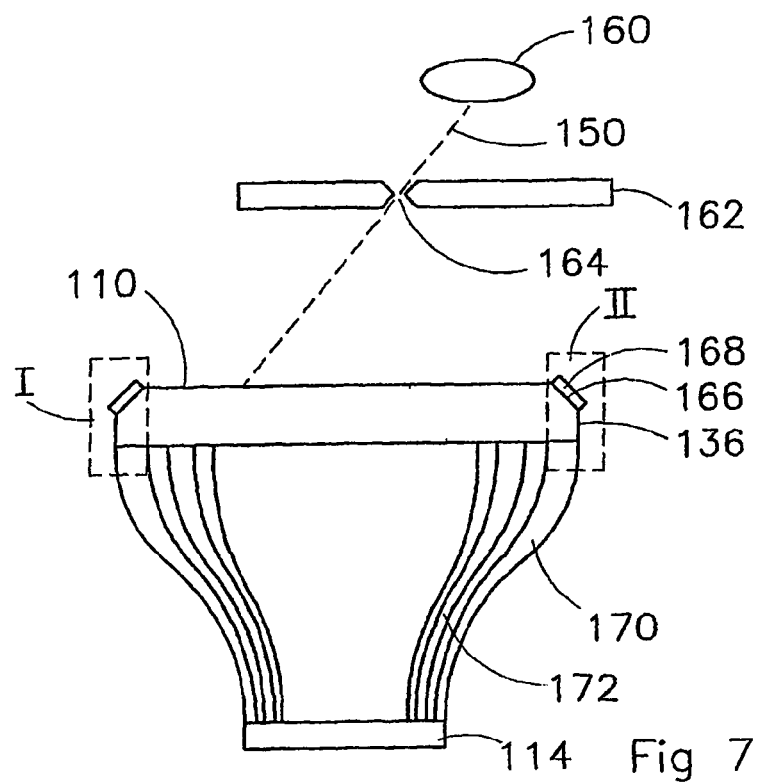
FIG. 7 shows a diagrammatic side view of a different embodiment.

FIG. 7 is a diagrammatic side view of another embodiment. In this figure, reference numeral 160 denotes a test animal with an isotope distribution, from which a gamma quant 150 impinges on scintillation material 110 through a pinhole 164 in a pinhole wall 162, on which scintillation material two lateral detectors I and II are arranged, indicated partly diagrammatically by a box with dotted lines. The lateral detectors I and II comprise a bevelled edge 166 of scintillation material and a radiation screen 168, as well as a light guide 170 towards a main detector 114. In addition, reference numeral 172 indicates a converging bundle of light guides.

The pinhole wall 162 is made of a material which substantially blocks the gamma radiation generated in source 60, except for a small opening or pinhole 164. The source 160 for example contains a test animal which has been administered a radioactive isotope which will spread inside the test animal. The emitted gamma radiation 150, or any other high-energy radiation, will be imaged via pinhole 164 onto the scintillation material 110 arranged at a suitable distance. Scintillation radiation will be generated there and conducted to the detector 114 via the light guide bundle 172 while retaining the position information. In this case, the light guide bundle 172 is a converging bundle so that the dimensions of the main detector 114 can be kept compact, which is advantageous for the costs and the quality of this detector 114. Of course, it is also possible to use a non-converging bundle.

The light guide 170 is also shown here as being converging and offers the same advantage, but may also be non-converging.

Incidentally, instead of a single light guide 170, it is also possible to use a bundle of light guides, which are, for example, more flexible than a single light guide, but as position information is not necessary with a subdetector or lateral detector I, II, a light guide bundle does not have to be position resolved either.

The lateral detectors I and II comprise a bevelled edge 166 of scintillation material 110 as optical element, which edge reflects the scintillation light to the light guide 170. The angle of the edge 166 may be approximately 45°, but of course this is not obligatory. In most cases, the scintillation material will have a refractive index which, at an angle of incidence of likewise approximately 45°, ensures total internal reflection. In other cases, a reflecting layer, made of metal, such as silver, for example, may be advantageous. Reference numeral 168 denotes a radiation screen which prevents gamma quants from landing via the bevelled edge on the scintillation material under the bevelled edge 166 and generating unwanted scintillation there. The radiation screen 168 is, for example, made of lead or the like. The bevelled edge 66 is shown here as being on a side edge of the scintillation material 110, but it may also be a corner.

FIGS. 8a and 8b diagrammatically show a first embodiment of a scanner 200 according to the invention, in a first and second position while an individual is being scanned.

In this case, 210 denotes a CT scanner having a CT-scanning space 212, 214 denotes a radionuclide scanner having a radio scanning space 216. A bed 218 with an individual 220 on it is situated in said spaces 212 and 216 and can be moved in the direction of the arrows C.

A left-hand screen is denoted by 222 and a right-hand screen, which also comprises the drive mechanism 226 of the bed, is denoted by 224. Furthermore, reference numeral 230 denotes a guide with a motor 232.

With regard to its embodiment, the CT scanner is not subject to any particular limitation and may be designed to perform a scan in which the bed 218 moves through the CT scanning space 212. The internal x-ray source and opposite detector can in this case move around the individual 220, and perform either a stepped scan (one rotation followed by displacement of the bed, etc.) or a helix scan, for example, in which the bed is constantly being moved along and the x-ray source and detector are constantly rotating around the individual 220 at the same time. In this embodiment, and with this application, an individual 220 is first subjected to a radionuclide scan, followed by a CT scan, which order is obviously dependent on the direction of movement through the scanner 200. Such a combination of a radionuclide scan with a CT scan is for example expedient when data from the radionuclide scan have to be correlated with physiological data of an individual 220, for example on the basis of data obtained by means of a CT scan.

Due to the CT scan, which uses relatively intense x-radiation, the bed is surrounded by a radiation screen 222, which is only indicated diagrammatically. In addition, a right-hand screen 224, indicated diagrammatically, is provided on the opposite end of the bed, which screen is, however, substantially always present and also comprises, for example, the bed drive mechanism 226. In principle, the right-hand screen 224 may comprise an optionally closable opening which adjoins the radioscan space 216 and through which the bed 218 may pass.

The illustrated drive mechanism 226 may, as mentioned above, move the support 218 in the direction of the arrows C, i.e. the direction of the support. In addition, the drive mechanism 226 can also move the support in one or more directions at right angles to the direction of the support. By displacing the support in this manner, in particular in the first detection space, but obviously also, if desired, in the second, it is possible to enlarge the object image field of the first, and if desired also the second, scanner. Effectively, it is thus possible to scan a different part of an object or individual 220, so that overall a larger volume can be scanned.

FIG. 8b shows the same device 200 as in FIG. 8a, but in a position in which only a radiological scanner 214 is used. The CT scanner 210 is moved upwards along the guide 230 by the drive mechanism 232 in such a manner that the CT scanner 210 leaves the radioscan space 216 completely free. It should be noted here that the CT scanner does not have to be moved as far upwards as illustrated in order to achieve this. Furthermore, the left-hand screen 222 is shown as being folded back, but it is also possible to provide this in the same manner as in FIG. 8a. The illustrated embodiment is suitable for performing a separate radionuclide scan, it being advantageous that the working space, that is to say the radioscan space 216, is readily accessible. This is not only expedient for the operator, as it is now readily possible to monitor the individual 218 or another object, but also for the individual or a test animal, as they now have an optimum sense of space.

FIGS. 9a and 9b diagrammatically show a front and side view, respectively, of an embodiment of the multiple image-forming device (scanner) according to the invention. In this case, as in the entire drawing, identical reference numerals denote similar components. In this case, the CT scanner is divided into two components, a part 210-a having an opening 234, and a part 210-b fitting in the opening.

The virtually continuous annular part 210-a is moved upwards in this case in order to give access to the radionuclide scanner 214, with part 210-b remaining behind. Part 210-a has an opening 234 with dimensions which make it possible to lower the part 210-a over the bed 218 during use of the scanner 200. Part 210-a may adjoin part 210-b, thus resulting in a continuous ring. Inside this ring, the x-ray source and the detector can then move around.

As a result, it is possible to decide even during a radionuclide scan, which in itself can take a relatively long time, to perform a CT scan on the object on the bed 218. This may be advantageous, for example, in order to collect additional data about the object, but only if this is deemed to be absolutely necessary. If this is not deemed necessary, the CT scanner can remain in its non-active position.

Incidentally, in another embodiment, it is possible to omit component 210-b. In that case, the body surrounding the second detection space of the CT scanner 210 consists of one part. This part may be a completely continuous annular shape in order to provide optimum radiation protection in the direction of the plane of the ring towards the outside. In this case, however, the CT scanner cannot give access to the support 218 if the support is situated in the second detection space. In another embodiment, this body comprises the component 210-a illustrated in FIG. 9a, with the component 210-b thus having been omitted. A structure is then incorporated in the component 210-a, for example, on which an internal displaceable second structure is situated with the x-ray source and/or x-ray detector on top thereof. By rotating said second structure inside component 210-a, i.e. about an axis through the centre of the ring and parallel to the support 218, the combination of x-ray source/x-ray detector will be able to perform the circular movement required for many types of scan. A suitable structure may comprise, for example, bearings or rollers and a motor as a guide and/or drive mechanism.

In addition, it is possible to provide the component 210-a with a displaceable screening part, in which the screening part can move in or over a section of component 210-a, in order to give access to an opening 234 in the component 210-a, for example while moving over the support, or in order to fill the opening 234, for example during scanning. All this is illustrated, for example, in FIG. 10, which shows a diagrammatic side view of a further embodiment of the multiple detection device according to a third aspect of the invention. Here, a support comprising a substantially vertical support bar 236 is shown, which can be moved relative to a support base 238. The radiation screening cover comprises a first part 224, which also comprises the CT scanner itself, and a second part 240. Both parts are guided over the support base 238 and can be displaced in the direction of the arrows C. In this case, a first, open position is illustrated by solid lines and a second, closed position by dashed lines. The second part 240 comprises, for example, a cover closed on one side, while the first part 224 comprises an opening which complements the outer circumference of the second part 240, viewed in the direction of the support. Thus, a telescopic radiation screen can be obtained, which can be very compact and still offers sufficient space to work with a test subject. In this case, it should be noted that the drawing is not to scale.

The illustrated embodiments relate to non-limiting embodiments of the invention. In particular technical features of the illustrated embodiments can also be combined or form alternatives. The scope of protection is defined by the attached claims.

The invention claimed is:

1. Scintillation detection device designed for detecting high-energy radiation, and comprising
    a scintillation material for converting incident high-energy radiation into optical scintillation radiation, the scintillation material comprising a front side facing a source of the high-energy radiation, a rear side located opposite the former, as well as at least one lateral surface which connects the front side and the rear side,
    a main detector located on the rear side of the scintillation material and designed for the position-sensitive detection of the scintillation radiation emitted by the rear side, and
    at least one lateral detector which is designed for detecting at least part of the scintillation radiation emitted by the lateral surface.

2. Scintillation detection device according to claim 1, comprising several lateral detectors arranged at mutually different positions around the lateral surface.

3. Scintillation detection device according to claim 2, in which the scintillation material comprises a substantially rectangular crystal, the lateral surface comprising at least one first and one second part surface,
    a first lateral detector of the plurality of lateral detectors being designed to detect the scintillation radiation emitted by the first part surface, and a second lateral detector of the plurality of lateral detectors being designed to detect the scintillation radiation emitted by the second part surface.

4. Scintillation detection device according to claim 3, in which the first and the second part surface are located opposite one another.

5. Scintillation detection device according to claim 1, in which the main detector comprises a two-dimensional detector.

6. Scintillation detection device according to claim 3, furthermore comprising a third and a fourth lateral detector, as well as a third and a fourth part surface, the third lateral detector being designed to detect scintillation radiation emitted by the third part surface, and the fourth lateral detector being designed to detect scintillation radiation emitted by the fourth part surface, the third and fourth part surface being located opposite one another.

7. Scintillation detection device according to claim 1, in which at least one lateral detector comprises several partial lateral detectors.

8. Scintillation detection device according to claim 1, in which at least one lateral detector comprises at least one additional subdetector sensitive to scintillation radiation.

9. Scintillation detection device according to claim 8, in which at least one lateral detector comprises an optical element which conducts the incident scintillation radiation to the subdetector.

10. Scintillation detection device according to claim 9, in which the subdetector is integral with the main detector.

11. Scintillation detection device according to claim 9, in which the optical element comprises at least one light guide which conducts the incident scintillation radiation to the subdetector.

12. Scintillation detection device according to claim 1, in which the main detector comprises a detector part which is sensitive to the optical radiation, as well as a series of light guides positioned between the rear side of the scintillation material and the detector part which is sensitive to optical radiation.

13. Scintillation detection device according to claim 1, in which the main detector comprises a CCD or a CMOS.

14. Scintillation detection device according to claim 1, in which the at least one lateral detector comprises a position-sensitive detector.

15. Scintillation detection device according to claim 14, in which the scintillation material comprises several layers.

16. Scintillation detection device according to claim 1, in which the at least one lateral detector is designed to carry out part measurements of the scintillation radiation with a lateral detection time for detecting which is at most half of the detection time of the main detector.

17. Scintillation detection device according to claim 1, furthermore comprising a pinhole located at the front side of the scintillation material.

18. Scintillation detection device according to claim 1, furthermore comprising a data-processing device, the data-processing device being designed for processing detected scintillation radiation.

19. Scintillation detection device according to claim 18, in which the data-processing device is designed to ignore the scintillation radiation detected by the main detector, if an amount of scintillation energy measured by at least one lateral detector of substantially simultaneously emitted scintillation radiation emitted by the lateral surface stays below a predetermined threshold value, stays below a predetermined first threshold value and exceeds a predetermined second threshold value, or exceeds a predetermined second threshold value.

20. Scintillation detection device according to claim 18, in which the data-processing device is designed for determining a position indication in the scintillation material of a source of the scintillation radiation with the aid of the at least one lateral detector.

21. Scintillation detection device according to claim 18, in which the data-processing device is designed for determining the number N of events in a measurement of the main detector, with the aid of the amount of scintillation energy detected by the at least one lateral detector or with the aid of the number of flashes in a specific energy range.

22. Scintillation detection device according to claim 21, to the extent that it is dependent, in which the data-processing device is designed for determining N from the number of part measurements in which the amount of scintillation energy detected by the at least one lateral detector exceeds a predetermined threshold value.

23. Scintillation detection device according to claim 21, in which the data-processing device is furthermore designed for determining a position indication for each of the N events in the scintillation material.

24. Method for detecting high-energy radiation, comprising the step of using the scintillation detection device according to claim 1.

25. Method according to claim 24, comprising providing a source of high-energy radiation;
    detecting scintillation radiation emitted by the rear side using the main detector during a measurement time, as well as detecting scintillation radiation emitted by the lateral surface using the at least one lateral detector;
    in which an event in the scintillation radiation detected by the main detector is ignored if an amount of scintillation energy associated with that event and detected by the lateral detector stays below a predetermined first threshold value or exceeds a predetermined second threshold value.

26. Method according to claim 24, comprising
    determining an event in the scintillation radiation detected by the main detector;
    determining an amount of scintillation energy associated with that event using the at least one lateral detector;
    determining from the amount of scintillation energy from which part of the scintillation material the scintillation radiation originated; and
    narrowing the scintillation radiation associated with that event and detected by the main detector to scintillation radiation detected by a part of the main detector associated with that part of the scintillation material.

27. Method according to claim 24, comprising
    determining the number of events N in the scintillation energy detected by the main detector using the at least one lateral detector;
    determining the N most likely separate events in the scintillation energy detected by the main detector.

28. Method according to claim 27, in which
    the scintillation detection device comprises at least two lateral detectors, each having a lateral detection time for detecting the scintillation radiation which is at most half the measurement time of the main detector,
    each of the lateral detectors being designed for carrying out at least two part measurements during the measurement time, and the method ignores an event if not at least two lateral detectors, and preferably all lateral detectors, detect a corresponding amount of scintillation energy.

* * * * *